United States Patent
Garvey et al.

(10) Patent No.: US 6,211,179 B1
(45) Date of Patent: Apr. 3, 2001

(54) NITROSATED AND NITROSYLATED PHOSPHODIESTERASE INHIBITOR COMPOUNDS, COMPOSITIONS AND THEIR USES

(75) Inventors: David S. Garvey, Dover, MA (US); Inigo Saenz de Tejada, Madrid (ES)

(73) Assignee: NitroMed, Inc., Bedford, MA (US)

(*) Notice: Subject to any disclaimer, the term of this patent is extended or adjusted under 35 U.S.C. 154(b) by 0 days.

(21) Appl. No.: 09/347,426

(22) Filed: Jul. 6, 1999

Related U.S. Application Data

(60) Division of application No. 09/145,142, filed on Sep. 1, 1998, now Pat. No. 5,958,926, and a continuation-in-part of application No. PCT/US97/19870, filed on Oct. 31, 1997, said application No. 09/142,142, is a continuation-in-part of application No. 08/740,764, filed on Nov. 1, 1996, now Pat. No. 5,874,437.

(51) Int. Cl.$^7$ .......................... A61K 31/519; A61K 31/52
(52) U.S. Cl. ................. 514/252.16; 514/258; 514/262; 544/254; 544/265; 544/280
(58) Field of Search .................. 514/252.16, 258

(56) References Cited

U.S. PATENT DOCUMENTS

| | | | |
|---|---|---|---|
| 4,308,278 | 12/1981 | Schneider et al. | 424/273 |
| 4,963,541 | 10/1990 | Brooks et al. | 514/183 |
| 5,171,217 | 12/1992 | March et al. | 604/53 |
| 5,190,967 | 3/1993 | Riley | 514/411 |
| 5,196,426 | 3/1993 | Saccomano et al. | 514/258 |
| 5,223,504 | 6/1993 | Noverla et al. | 514/263 |
| 5,254,575 | 10/1993 | Pick et al. | 514/365 |
| 5,340,827 | 8/1994 | Beeley et al. | 514/352 |
| 5,346,901 * | 9/1994 | Bell et al. | 514/258 |
| 5,380,758 | 1/1995 | Stamler et al. | 514/562 |
| 5,426,107 | 6/1995 | Bell et al. | 514/234.2 |
| 5,438,060 | 8/1995 | Miyazaki et al. | 514/258 |
| 5,439,938 | 8/1995 | Snyder et al. | 514/565 |
| 5,491,147 | 2/1996 | Boyd et al. | 514/247 |
| 5,492,911 | 2/1996 | Stief | 514/252 |
| 5,543,430 | 8/1996 | Kaesemeyer | 514/565 |
| 5,545,647 | 8/1996 | Tanaka et al. | 514/343 |
| 5,565,466 | 10/1996 | Gioco et al. | 514/280 |
| 5,583,101 | 12/1996 | Stamler et al. | 514/562 |
| 5,618,814 | 4/1997 | Heckel et al. | 514/234.2 |
| 5,631,284 * | 5/1997 | Legzdins et al. | 514/505 |
| 5,645,839 | 7/1997 | Chobanian et al. | 424/400 |
| 5,646,181 | 7/1997 | Fing et al. | 514/506 |
| 5,698,589 | 12/1997 | Allen | 514/509 |
| 5,731,339 * | 3/1998 | Lowrey | 514/400 |
| 5,767,160 | 6/1998 | Kaesmeyer | 514/565 |
| 5,824,669 * | 10/1998 | Garvey et al. | 514/174 |
| 5,861,404 | 1/1999 | Niewohner et al. | 514/262 |
| 5,877,216 | 3/1999 | Place et al. | 514/573 |
| 5,932,538 * | 8/1999 | Garvey et al. | 514/2 |
| 5,973,011 * | 10/1999 | Noack et al. | 514/724 |
| 6,007,824 * | 12/1999 | Duckett et al. | 424/195.1 |
| 6,037,346 * | 3/2000 | Doherty, Jr. et al. | 514/258 |

FOREIGN PATENT DOCUMENTS

| | | |
|---|---|---|
| 0252721 | 1/1988 | (EP) . |
| 0 352 960 | 1/1990 | (EP) . |
| 0442204 | 8/1991 | (EP) . |
| 0 463 756 | 1/1992 | (EP) . |
| 463756 | 1/1992 | (EP) . |
| 0506194 | 9/1993 | (EP) . |
| 2547501 | 12/1984 | (FR) . |
| 9306103 | 4/1993 | (WO) . |
| 9312068 | 6/1993 | (WO) . |
| 9501338 | 1/1995 | (WO) . |
| 9509636 | 4/1995 | (WO) . |
| WO 95/26725 * | 10/1995 | (WO) . |
| 9526768 | 10/1995 | (WO) . |
| 96 25184 | 8/1996 | (WO) . |
| 9734871 | 9/1997 | (WO) . |
| 9739760 | 10/1997 | (WO) . |
| 9819672 | 5/1998 | (WO) . |

OTHER PUBLICATIONS

Boolell et al, British Journal of Urology, 78(2):257–261 (1996).

Martel et al, Drugs of the Future, 22(2):138–143 (1997).

Chemical Abstracts, vol. 125, No. 15, Abstract No. 191382 (Oct. 7, 1996).

Chemical Abstracts, vol. 123, No. 1, Abstracts No. 574 (Jul. 3, 1995).

Chemical Abstracts, vol. 120, No. 25, Abstract No. 315630 (Jun. 20, 1994).

Chemical Abstracts, vol. 121, No. 7, Abstract No. 73410 (Aug. 15, 1994).

Chemical Abstracts, vol. 116, No. 1, Abstract No. 4477 Jan. 6, 1992).

Brown et al. Chemical Abstracts, 120(1):612, Abstract 5451d (1994).

Chen et al, *BJU International*, 83:269–273 (1999).

(List continued on next page.)

*Primary Examiner*—Mukund J. Shah
*Assistant Examiner*—Deepak R. Rao
(74) *Attorney, Agent, or Firm*—Hale and Dorr LLP

(57) ABSTRACT

Disclosed are nitrosated and/or nitrosylated phosphodiesterase inhibitors having the formula NO$_n$-PDE inhibitor where n is 1 or 2. The invention also provides compositions comprising such compounds in a pharmaceutically acceptable carrier. The invention also provides a composition comprising a therapeutically effective amount of an phosphodiesterase inhibitor (PDE inhibitor), which can optionally be substituted with at least one NO or NO$_2$ moiety, and one to ten fold molar excess of a compound that donates, transfers or releases nitrogen monoxide as a charged species, i. e., nitrosonium (NO$^+$) or nitroxyl (NO$^-$), or as the neutral species, nitric oxide (NO•) or which stimulates endogenous EDRF production. The invention also provides compositions comprising such compounds in a pharmaceutically acceptable carrier. The invention also provides methods for treating sexual dysfunctions in males and females.

28 Claims, 30 Drawing Sheets

OTHER PUBLICATIONS

Boolell et al, *International Journal of Impotence Research*, 8:47–52 (1996).

Krane et al, *New England Journal of Medicine*, 321(24):1648–1659 (1989).

Trigo–Tocha et al, *Neurourol. Urodyn.*, 13(1):71–80 (1994).

Sparwasser et al, *J. Urol.*, 152:6, Pt. 1, pp. 2159–2163 (1994).

Zorgniotti et al, *Int. J. Impotence Res.*, 6:33–36 (1994).

Terrett et al, *Bioorg. Med. Chem. Lett.*, 6(15):1819–1824 (1996).

Park et al, *Biochem. Biophys. Res. Commun.*, 249(3):612–617 (1998).

Mathers et al, *European Urology*, 35(suppl 2):67 (abstract 266) (1999).

\* cited by examiner

NITROSATED AND NITROSYLATED PHOSPHODIESTERASE INHIBITOR COMPOUNDS, COMPOSITIONS AND THEIR USES

RELATED APPLICATIONS

This is a divisional of U.S. application Ser. No. 09/145,142 filed Sep. 1, 1998, issued as U.S. Pat. No. 5,958,926, which is a continuation-in-part of U.S. application Ser. No. 08/740,764, filed Nov. 1, 1996, issued as U.S. Pat. No. 5,874,437; and which is a continuation-in-part of PCT/US97/19870 filed Oct. 31, 1997.

FIELD OF THE INVENTION

This invention generally relates to pharmaceuticals and more specifically to methods and compositions for treating sexual dysfunctions in males and females.

BACKGROUND OF THE INVENTION

Adequate sexual function is a complex interaction of hormonal events and psychosocial relationships. There are four stages to sexual response as described in the *International Journal of Gynecology & Obstetrics*, 51(3):265–277 (1995). The first stage of sexual response is desire. The second stage of sexual response is arousal. Both physical and emotional stimulation may lead to breast and genital vasodilation and clitoral engorgement (vasocongestion). In the female, dilation and engorgement of the blood vessels in the labia and tissue surrounding the vagina produce the "orgasmic platform," an area at the distal third of the vagina where blood becomes sequestered. Localized perivaginal swelling and vaginal lubrication make up the changes in this stage of sexual response. Subsequently, ballooning of the proximal portion of the vagina and elevation of the uterus occurs. In the male, vasodilation of the cavernosal arteries and closure of the venous channels that drain the penis produce an erection. The third stage of sexual response is orgasm, while the fourth stage is resolution. Interruption or absence of any of the stages of the sexual response cycle can result in sexual dysfunction. One study found that 35% of males and 4:2% of females reported some form of sexual dysfunction. Read et al, *J. Public Health Med.*, 19(4):387–391 (1997).

In both pre-menopausal and menopausal females, sexual dysfunction can include, for example, sexual pain disorders, sexual desire disorders, sexual arousal dysfunction, orgasmic dysfunction, dyspareunia, and vaginismus. Sexual dysfunction can be caused, for example, by pregnancy, menopause, cancer, pelvic surgery, chronic medical illness or medications.

Erectile dysfunction is a widespread disorder that is thought to affect about 10% to 15% percent of adult men. A number of causes of erectile insufficiency, in addition to anatomical deficiencies of the penis or scrotum that preclude an erection sufficient for vaginal penetration, have been identified. Causes of erectile dysfunction can be categorized as psychogenic, neurogenic, endocrinologic, drug-induced, or vasculogenic and in any individual suffering from erectile dysfunction there may be more than one cause.

Psychogenic impotence is often the result of anxiety or depression, with no apparent somatic or organic impairment. Neurogenic impotence may arise from, for example, surgery or a pelvic injury, involving the nervous system affecting the penis. Erectile dysfunction which is endocrinologic in origin is most often associated with the disorders hypo- or hypergonadotropic hypogonadism and hyperprolactinemia.

Vasculogenic impotence is thought to be the most frequent cause of impotence accounting for approximately fifty percent of all cases of organic impotence. In these cases, the erectile dysfunction may be attributed to alterations in the flow of blood to and from the penis. Atherosclerotic or traumatic arterial occlusive disease to the arteries which supply blood to the penis can lead to a decrease in the rigidity of the erect penis as well as increase the time to achieving maximal erection. In still other cases, there is leakage from veins in the penis such that sufficient pressure for an erection can be neither obtained nor maintained.

There is also a high incidence of erectile insufficiency among diabetics, particularly those with insulin-dependent diabetes mellitus. Erectile dysfunction in diabetics is often classified as "diabetogenic," although the underlying dysfunction is usually neurogenic, but may be vasculogenic or neurogenic and vasculogenic. About half of diabetic males suffer from erectile insufficiency, and about half of the cases of neurogenic impotence are in diabetics.

Erectile insufficiency is sometimes a side effect of certain drugs, such as beta-antagonists that are administered to reduce blood pressure in persons suffering from hypertension, or drugs administered to treat depression or anxiety. Excessive alcohol consumption has also been linked to erectile insufficiency. These forms of erectile insufficiency may be regarded as a subset of neurogenic or psychogenic insufficiency.

A number of methods to treat impotence are available. These treatments include pharmacological treatments, surgery and, in cases of psychogenic dysfunction, psychological counseling is sometimes effective. Psychogenic impotence often can be cured by counseling coupled with a demonstration to the patient that he is capable of having a full erection by inducing such an erection from one to a few times in the patients. Insufficiency due to excessive alcohol consumption is sometimes cured by reducing or eliminating such consumption.

In the rare cases where the insufficiency is untreatable because of venous leakage, surgery can usually be used to repair the venous lesion and thereby either cure the insufficiency or, if there remains an erectile insufficiency after repair of the venous lesion, render the insufficiency amenable to treatment by pharmacological methods. Also, penile implants, which provide a mechanic means to produce an erection sufficient for vaginal penetration, are widely used to treat impotence. In recent years, implants have been used, especially in cases where pharmacological intervention is ineffective, which are usually cases of severe vasculogenic impotence. Treatment of impotence with penile implants, however, entails serious disadvantages. Such treatment requires surgery and necessitates total destruction of the erectile tissues of the penis, forever precluding normal erection.

Pharmacological methods of treatment are also available. Such methods, however, have not proven to be highly satisfactory or without potentially severe side-effects. Papaverine is now widely used to treat impotence, although papaverine is ineffective in overcoming impotence due, at least in part, to severe atherosclerosis. Papaverine is effective in cases where the dysfunction is psychogenic or neurogenic and severe atherosclerosis is not involved. Injection of papaverine, a phosphodiesterase inhibitor and a smooth muscle relaxant, or phenoxybenzamine, a nonspecific antagonist and hypotensive, into corpus cavernosum has been found to cause an erection sufficient for vaginal penetration, however, these treatments are not without the serious and often painful side effect of priapism. Also, in cases where severe atherosclerosis is not a cause of the dysfunction, intracavernosal injection of phentolamine, an a-adrenergic antagonist, causes an erection sufficient for vaginal. penetration. The resulting erection is one of significantly shorter duration than that induced by intracavernosal injection of papaverine or phenoxybenzamine and often times is of such short duration that satisfactory sexual relations are difficult or impossible. As an alternative or, in some cases an adjunct to phosphodiesterase inhibition or α-adrenergic blockade for the treatment of erectile dysfunction, prostaglandin E1 (PGE1) has been administered via intracavernosal injection. A major side effect frequently associated with intracorprally delivered PGE1 is penile pain and burning.

Thus, there is a need in the art for treatments of male and female sexual dysfunctions, including treatments without the undesirable side effects of those agents currently used. The present invention is directed to these, as well as other, important ends.

SUMMARY OF THE INVENTION

Nitric oxide (NO) has been shown to mediate a number of actions including the bactericidal and tumoricidal actions of macrophages and blood vessel relaxation of endothelial cells. NO and NO donors have also been implicated as mediators of nonvascular smooth muscle relaxation. As described herein, this effect includes the dilation of the corpus cavemosum smooth muscle, an event involved in the sexual response process in both males and females. However, the effects of modified phosphodiesterase inhibitors which are directly or indirectly linked with a nitric oxide adduct have not been investigated.

In the process of arriving at the present invention it was recognized that the risk of toxicities and adverse effects that are associated with high doses of phosphodiesterase inhibitors can be avoided by the use of such phosphodiesterase inhibitors when nitrosated or nitrosylated. Such toxicities and adverse effects include hypotension, syncope, as well as priapism. The smooth muscle relaxant properties of phosphodiesterase inhibitors and of compounds that donate, release or transfer nitrogen monoxide or elevate levels of endogenous endothelium-derived relaxing factor (EDRF) work together to permit the same efficacy with lower doses of the phosphodiesterase inhibitors.

Accordingly, in one aspect the invention provides novel nitrosated and nitrosylated phosphodiesterase inhibitors: $NO_n$-PDE inhibitor where n is 1 or 2. The phosphodiesterase inhibitor can be nitrosylated or nitrosated through sites such as oxygen (hydroxyl condensation), sulfur (sulfhydryl condensation), carbon and nitrogen. The invention also provides compositions comprising such compounds in a pharmaceutically acceptable carrier.

In another aspect the invention provides compositions comprising a therapeutically effective amount of at least one phosphodiesterase inhibitor (PDE inhibitor), which can optionally be substituted with at least one NO or $NO_2$ moiety, and one to ten fold molar excess of at least one compound that donates, transfers or releases nitrogen monoxide as a charged species, i.e., nitrosonium ($NO^+$) or nitroxyl ($NO^-$), or as the neutral species, nitric oxide (NO•), or elevates levels of endogenolis EDRF. The invention also provides compositions comprising such compounds in a pharmaceutically acceptable carrier.

In another aspect, the invention provides methods for treating and/or preventing sexual dysfunctions or improving and/or enhancing sexual responses in humans, including males and females, which comprises administering to an individual in need thereof a therapeutically effective amount of at least one nitrosated or nitrosylated PDE inhibitor.

In another aspect, the invention provides methods for treating and/or preventing sexual dysfunctions or improving and/or enhancing sexual responses in humans, including males and females, which comprises administering to an individual in need thereof a composition comprising a therapeutically effective amount of at least one PDE inhibitor which can optionally be substituted with at least one NO or $NO_2$ moiety, and at least one compound that donates, transfers or releases nitric oxide as a charged species, i.e., nitrosonium ($NO^+$) or nitroxyl ($NO^-$), or as the neutral species, nitric oxide (NO•), or that elevates levels of endogenous EDRF. The PDE inhibitor or PDE inhibitor directly or indirectly linked to at least one NO or $NO_2$ group, and nitric oxide donor can be administered separately or as components of the same composition.

The nitrosated or nitrosylated PDE inhibitor and the compound that donates, transfers or releases nitric oxide and/or stimulates endogenous production of NO or EDRF in vivo can be administered separately or as components of the same composition in one or more pharmaceutically acceptable carriers.

BRIEF DESCRIPTION OF THE DRAWINGS

The following drawings are illustrative of embodiments of the invention and are not intended to limit the scope of the invention as defined by the claims.

DETAILED DESCRIPTION OF THE INVENTION

Figure 1:
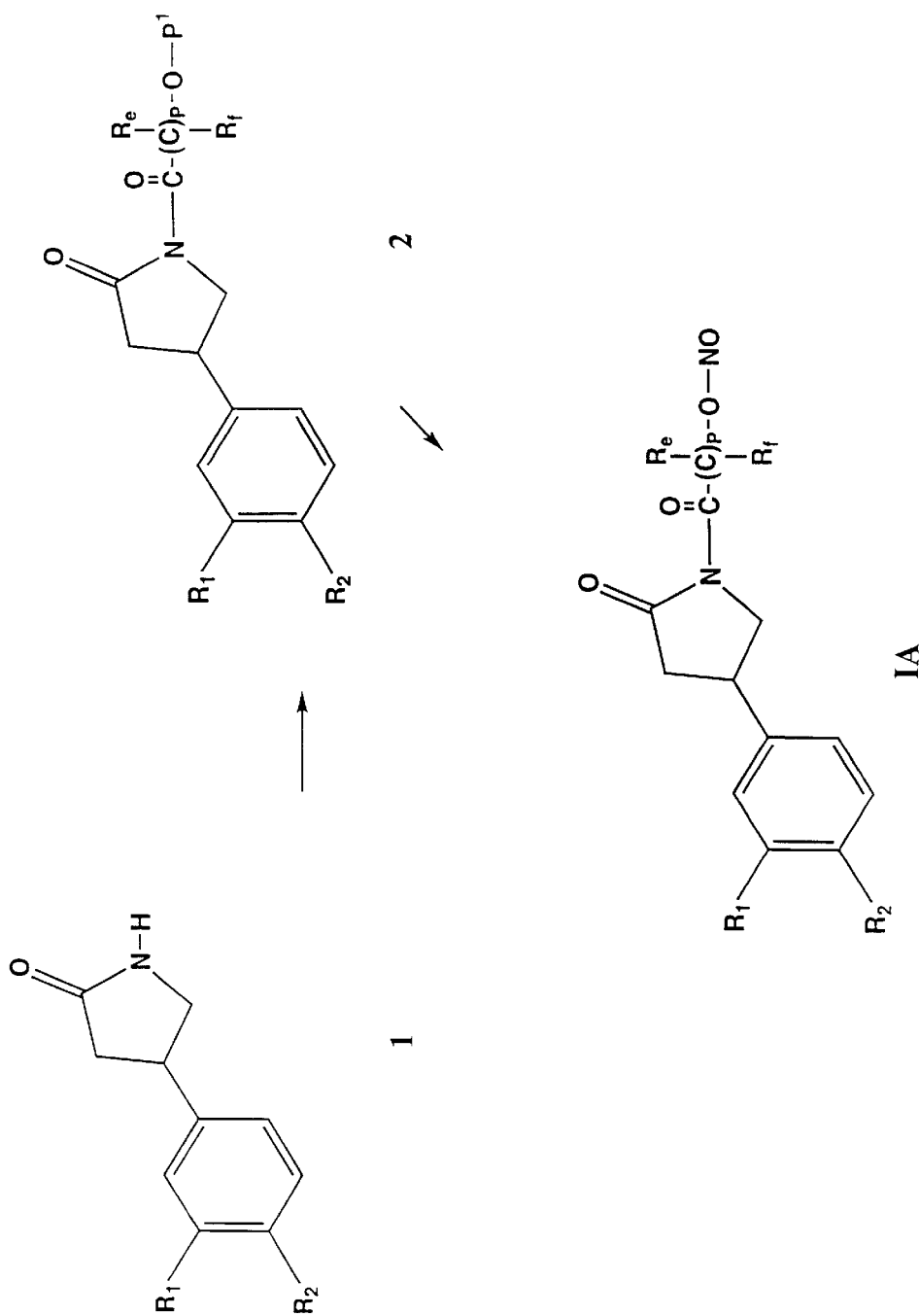
FIG. 1 shows a synthetic scheme for the preparation of nitrite containing substituted benzene derivatives.

The following definitions may be used throughout the specification.

The term "lower alkyl" as used herein refers to branched or straight chain alkyl groups comprising one to ten carbon atoms, including methyl, ethyl, propyl, isopropyl, n-butyl, t-butyl, neopentyl and the like.

The term "alkoxy" as used herein refers to $R_{50}O$— wherein $R_{50}$ is a lower alkyl group as defined herein. "Alkoxy groups" include, for example, methoxy, ethoxy, t-butoxy and the like.

The term "alkoxyalkyl" as used herein refers to an alkoxy group as previously defined appended to an alkyl group as previously defined. Examples of alkoxyalkyl include, but are not limited to, methoxymethyl, methoxyethyl, isopropoxymethyl and the like.

The term "hydroxy" as used herein refers to —OH.

The term "hydroxyalkyl" as used herein refers to a hydroxy group as previously defined appended to a lower alkyl group as previously defined.

The term "alkenyl" as used herein refers to a branched or straight chain $C_2$–$C_{10}$ hydrocarbon which also comprises one or more carbon-carbon double bonds.

The term "amino" as used herein refers to —$NH_2$.

The term "nitrate" as used herein refers to —O—$NO_2$.

The term "alkylamino" as used herein refers to $R_{50}NH$— wherein $R_{50}$ is as defined in the specification. Alkylamino groups include, for example, methylamino, ethylamino, butylamino, and the like.

The term "dialkylamino" as used herein refers to $R_{52}R_{53}N$— wherein $R_{52}$ and $R_{53}$ are independently selected from lower alkyl groups as defined herein. Dialkylamino groups include, for example dimethylamino, diethylamino, methyl propylamino and the like.

The term "nitro" as used herein refers to the group —$NO_2$ and "nitrosated" refers to compounds that have been substituted therewith.

The term "nitroso" as used herein refers to the group —NO and "nitrosylated" refers to compounds that have been substituted therewith.

The term "aryl" as used herein refers to a mono- or bi-cyclic carbocyclic ring system having one or two aromatic rings including, but not limited to, phenyl, naphthyl, tetrahydronaphthyl, indanyl, indenyl, and the like. Aryl groups (including bicyclic aryl groups) can be unsubstituted or substituted with one, two or three substituents independently selected from lower alkyl, haloalkyl, alkoxy, amino, alkylamino, dialkylamino, hydroxy, halo, and nitro. In addition, substituted aryl groups include tetrafluorophenyl and pentafluorophenyl.

The term "alkylaryl" as used herein refers to a lower alkyl radical to which is appended an aryl group. Arylalkyl groups include, for example, benzyl, phenylethyl, hydroxybenzyl, fluorobenzyl, fluorophenylethyl and the like.

The term "arylalkoxy" as used herein refers to an alkoxy radical to which is appended an aryl group. Arylalkoxy groups include, for example, benzyloxy, phenylethoxy, chlorophenylethoxy and the like.

The term "cycloalkyl" as used herein refers to an alicyclic group comprising from about 3 to about 7 carbon atoms including, but not limited to, cyclopropyl, cyclobutyl, cyclopentyl, cyclohexyl and the like.

The term "bridged cycloalkyl" as used herein refers to two or more cycloalkyl radicals fused via adjacent or non-adjacent carbon atoms, including, but not limited to, adamantyl and decahydronapthyl.

The term "cycloalkoxy" as used herein refers to $R_{54}O$— wherein $R_{54}$ is cycloalkyl as defined in this specification. Representative examples of alkoxy groups include cyclopropoxy, cyclopentyloxy, and cyclohexyloxy and the like.

The term "arylthio" as used herein refers to $R_{55}S$— wherein $R_{55}$ is an aryl group as defined herein.

The term "alkylsulfinyl" as used herein refers to $R_{50}$—S$(O)_2$— wherein $R_{50}$ is as defined in this specification.

The term "caboxamido" as used herein refers to —C(O)$NH_2$.

The term "carbamoyl" as used herein refers to —O—C(O)$NH_2$.

The term "carboxyl" as used herein refers to —$CO_2H$.

The term "carbonyl" as used herein refers to —C(O)—.

The term "halogen" or "halo" as used herein refers to I, Br, Cl, or F.

The term "haloalkyl" as used herein refers to a lower alkyl radical to which is appended one or more halogens. Representative examples of haloalkyl group include trigluoromethyl, chloromethyl, 2-bromobutyl, 1-bromo-2-chloro-pentyl and the like.

The term "haloalkoxy" as used herein refers to a haloalkyl radical as defined herein to which is appended an alkoxy group as defined herein. Representative examples of haloalkoxy groups include 1,1,1-trichloroethoxy, 2-bromobutoxy and the like.

The term "heteroayl" as used herein refers to a mono-or bi-cyclic ring system containing one or two aromatic rings and containing at least one nitrogen, oxygen, or sulfur atom in an aromatic ring. Heteroaryl groups (including bicyclic heteroaryl groups) can be unsubstituted or substituted with one, two or three substituents independently selected from lower alkyl, haloalkyl, alkoxy, amino, alkylamino, dialkylamino, hydroxy, halo and nitro. Examples of heteroaryl groups include, but are not limited to, pyridine pyrazine, pyrimidine, pyridazine, pyrazole, triazole, thiazole, isothiazole, benzothiazole, benzoxazole, thiadiazole, oxazole, pyrrole, imidazole, isoxazole and the like.

The term "heterocyclic ring" as used herein refers to any 3-, 4-, 5-, 6-, or 7-membered nonaromatic ring containing at least one nitrogen atom, oxygen ator, or sulfur atom which is bonded to an atom which is not part of the heterocyclic ring.

The term "arylheterocyclic ring" as used herein refers to a bi- or tri-cyclic ring comprised of an aryl ring as previously defined appended via two adjacent carbon atoms of the aryl group to a heterocyclic ring as previously defined.

The term "heterocyclic compounds" as used herein refers to mono- and poly-cyclic compounds containing at least one heteroaryl or heterocyclic ring, as defined herein.

The term "amido" as used herein refers to —NH—C(O)—$R_{56}$ wherein $R_{56}$ is a lower alkyl, aryl, or hereroaryl group, as defined herein.

The term "alkylamido" as used herein refers to $R_{50}$N—C(O)—$R_{56}$ wherein $R_{50}$ is a lower alkyl group as defined herein and $R_{56}$ is a lower akyl, aryl, or hereroaryl group, as defined herein.

The term "carboxylic ester" as used herein refers to —C(O)O$R_{50}$, wherein $R_{50}$ is a lower alkyl group as defined herein.

The term "carboxylic acid" as used herein refers to —C(O)OH.

The term "phosphoryl" as used herein refers to —P($R_{70}$)($R_{71}$), wherein $R_{70}$ is a lone pair of electrons, sulfur or oxygen and $R_{71}$ is independently a hydrogen, a lower alkyl, an alkoxy, an alkylamino, a hydroxy or an aryl.

The term "sexual dysfunction" generally includes any sexual dysfunction in an animal, preferably a mammal, more preferably a human. The animal can be male or female. Sexual dysfunction may include, for example, sexual desire disorders, sexual arousal disorders, orgasmic disorders and sexual pain disorders. Female sexual dysfunction refers to any female sexual dysfunction including, for example, sexual desire disorders, sexual arousal dysfunction, orgasmic dysfunction, sexual pain disorders, dyspareunia, and vaginismus. The female can be pre-menopausal or menopausal. Male sexual dysfunction refers to any male sexual dysfunction including, for example, male erectile dysfunction and impotence.

While there are obvious differences in the sexual response between males and females, one common aspect of the sexual response is the erectile response. As described in U.S. Pat. No. 5,565,466, the disclosure of which is incorporated herein by reference in its entirety, the erectile response in both males and females is the result of engorgement of the erectile tissues of the genitalia with blood caused by the relaxation of smooth muscles in the arteries serving the genitalia.

The vasculature which serves erectile tissue in males and females is similar. In particular, the arterial circulation of the erectile tissues of the genitalia derives from the common iliac artery which branches from the abdominal aorta. The common iliac artery bifurcates into the internal and external iliac arteries. The internal pudic artery arises from the smaller of two terminal branches of the anterior trunk of the internal iliac artery. In the female, the internal pudic artery branches into the superficial perineal artery which supplies the labia pudenda. The internal pudic artery also branches into the artery of the bulb which supplies the bulbi vestibuli and the erectile tissue of the vagina. The artery of the corpus cavemosum, another branch of the internal pudic artery supplies the cavernous body of the clitoris. Still another branch of the internal pudic artery is the arteria dorsalis clitoridis which supplies the dorslm of the clitoris and terminates in the glans and membranous folds surrounding the clitoris which correspond to the prepuce of the male.

In the male, the internal pudic artery branches into the dorsal artery of the penis (which itself branches into a left and right branch) and the artery of the corpus cavemosum, all of which supply blood to the corpus cavernosum. The dorsal artery of the penis is analogous to the artery dorsalis clitoridis in the female, while the artery of the corpus cavernosum in the male is analogous to the artery of the same name in the female.

The male erectile response is regulated by the autonomic nervous system which controls blood flow to the penis via the interaction of peripheral nerves associated with the arterial vessels in and around the corpus cavernosum. In the non-aroused or non-erect state, the arteries serving the corpus cavernosum are maintained in a relatively constricted state, thereby limiting the blood flow to the corpus cavernosum. In the aroused state, the smooth muscles associated with the arteries relax and blood flow to the corpus cavernosum greatly increases, causing expansion and rigidity of the penis. Smooth muscle contraction opens valves through which blood can flow from the corpus cavernosum into the extracavernosal veins. When the relevant smooth muscles relax, the valves close diminishing venous outflow from the corpus cavernosum. When accompanied by increased arterial blood flow into the corpus cavernosum, this results in engorgement of the corpus cavernosum and an erection.

The pre-orgasmic sexual response in females can be broken down into distinct phases. Both the excitement phase and the plateau phase involve vasodilation and engorgement (vasocongestion) of the genitalia with arterial blood in a manner analogous to the male erectile response.

The excitement phase of the female sexual response is characterized by vasocongestion in the walls of the vagina which leads to the transudation of vaginal fluids and vaginal lubrication. Further, the inner one-third of the vaginal barrel expands and the cervix and the body of the uterus become elevated. This is accompanied by the flattening and elevation of the labia majora and an increase in clitoral size.

The plateau phase follows the excitement phase in the female sexual response and is characterized by prominent vasocongestion in the outer one-third of the vagina, causing a narrowing of the opening of the vagina and a retraction of the shaft and the glans of the clitoris against the symphysis pubis. These responses are also accompanied by a marked vasocongestion of the labia.

The vasocongestive aspects of the female sexual response are not restricted, to the genitalia in that areolar engorgement also occurs, sometimes to the extent that it masks the antecedent nipple erection that usually accompanies the excitement phase.

The vasodilation and vasocongestive responses may also be induced by pharmacological action without psychological stimulation or arousal by the female. Similarly, the male sexual response may also be induced by pharmacological action without psychological stimulation or arousal.

The present invention is directed to the treatment and/or prevention of sexual dysfunctions in animals, including males and females, by administering the compounds and compositions described herein. The present invention is also directed to improving and/or enhancing the sexual response in animals, including males and females, by administering the compounds and/or compositions described herein. The novel compounds and novel compositions of the present invention are described in more detail below.

Contemplated PDE inhibitors for use in the present invention include, for example, dipyridamole, zaprinast, sildenafil, filaminast, denbufyllene, piclamilast, zardaverine, rolipram and the like.

Sources of information for the above include Goodman and Gilman, The Pharmacological Basis of Therapeutics (9th Ed.), McGraw-Hill, Inc. (1996), The Physician's Desk Reference (49th Ed.), Medical Economics (1995), Drug Facts and Comparisons (1993 Ed), Facts and Comparisons (1993), and The Merck Index (12th Ed.), Merck & Co., Inc. (1996), the disclosures of each of which are incorporated herein by reference in their entirety.

A principal aspect of the invention relates to novel nitrosated and/or itrosylated phosphodiesterase inhibitors.

One embodiment of the invention provides compounds having structure I:

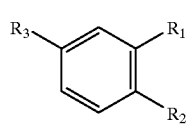

I wherein $R_1$ is an alkoxy, a cycloalkoxy, a halogen, or

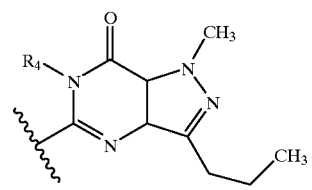

$R_2$ is a hydrogen, an alkoxy, or a haloalkoxy; and $R_3$ is:

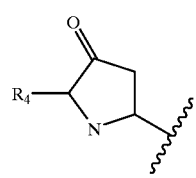

(i)

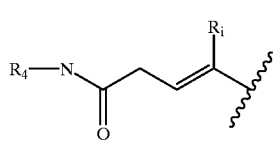

(ii)

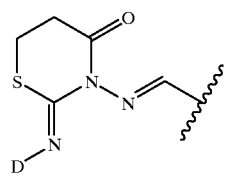

(iii)

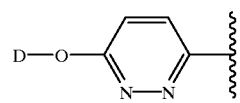

(iv)

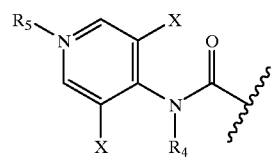

(v)

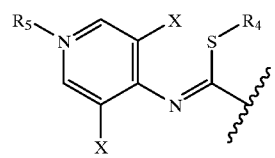

(vi)

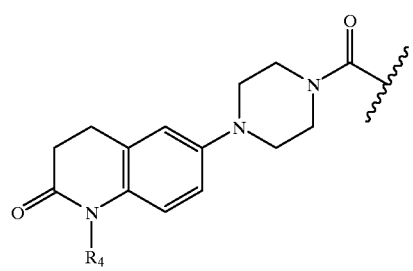

(vii)

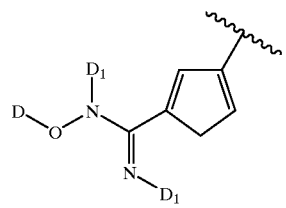

(viii)

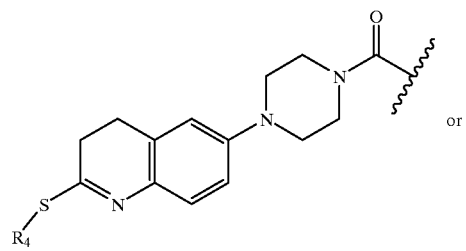

(ix)

or

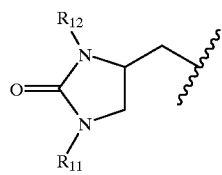

wherein

D is (i) —NO, (ii) —NO$_2$, (iii) —C(R$_d$)—O—C(O)—Y—Z—(C(R$_e$)(R$_f$))$_p$—T—Q, wherein R$_d$ is a hydrogen, a lower alkyl, a cycloalkyl, an aryl, an arylalkyl, or a heteroaryl; Y is oxygen, sulfur, carbon or NR$_i$, wherein R$_i$ is a hydrogen or a lower alkyl; R$_e$ and R$_f$ are each independently a hydrogen, a lower alkyl, a haloalkyl, an alkoxy, a cycloalkyl, an aryl, a heteroaryl, an arylalkyl, an amino, an alkylamino, an amido, an alkylamido, a dialkylamino, a carboxylic acid, a carboxylic ester, a carboxamido or —T—Q, or R$_e$ and R$_f$ taken together are a carbonyl, a cycloalkyl, a heterocyclic ring or a bridged cycloalkyl; p is an integer from 1 to 10; T is independently a covalent bond, oxygen, sulfur or nitrogen; Z is a covalent bond, a lower alkyl, a haloalkyl, a cycloalkyl, an aryl, a heteroaryl, an arylalkyl, a heteroalkyl, an arylheterocyclic ring or (C(R$_e$)(R$_f$))$_p$; and Q is —NO or —NO$_2$; (iv) —C(O)—Y—Z—(G—(C(R$_e$)(R$_f$))$_q$—T—Q)$_p$, wherein G is a covalent bond, —T—C(O)—, —C(O)—T— or T, wherein q is an integer from 0 to 5, and Y, Z, R$_e$, R$_f$, p, T and Q are as defined above; or (v) —P—Z—(G—(C(R$_e$)(R$_f$))$_q$—T—Q)$_p$, wherein P is a carbonyl, a phosphoryl or a silyl, and Z, G, p, q, T, Q, R$_e$ and R$_f$ are as defined above;

R$_4$ is (i) hydrogen, (ii) —C(R$_d$)—O—C(O)—Y—Z—(C(R$_e$)(R$_f$))$_p$—T—Q, (iii)—C(O)—T—(C(R$_e$)(R$_f$))$_p$—T—Q, or (iv) —C(O)—Z—(G—(C(R$_e$)(R$_f$))$_p$—T—Q)$_p$; and wherein R$_d$, R$_e$, R$_f$, p, G, T, Q, Y, and Z are defined above;

R$_5$ is a lone pair of electrons or —C(R$_d$)—O—C(O)—Y—Z—(C(R$_e$)(R$_f$))$_p$—T—Q wherein R$_d$, R$_e$, R$_f$, p, T, Q, Y, and Z are defined above;

R$_{11}$ and R$_{12}$ are independently selected from hydrogen or R$_4$, wherein R$_4$ is as defined above with the proviso that R$_{11}$ and R$_{12}$ are not both hydrogen;

X is a halogen, and D$_1$ is D or hydrogen, wherein D is as defined above.

Another embodiment of the invention provides compounds having structure II:

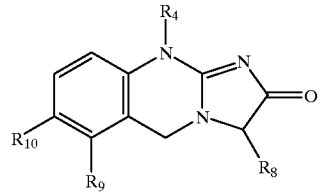

wherein R$_4$ is defined above;

R$_8$ is a hydrogen or a lower alkyl;

R$_9$ is a hydrogen or a halogen; and

R$_{10}$ is:

(i) hydrogen,

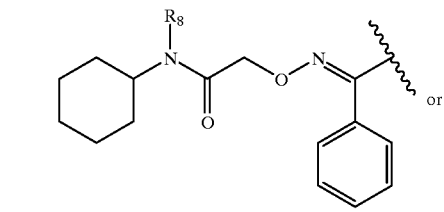

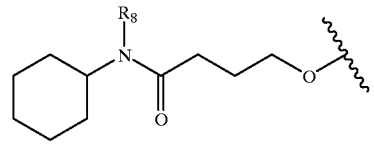

wherein R$_8$ is as defined above.

Another embodiment of the invention provides compounds having structure

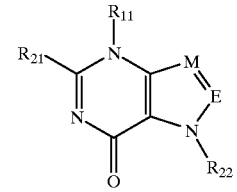

wherein,

E is nitrogen or —CH—;

M is nitrogen or —C(R$_8$)—;

R$_{21}$ is:

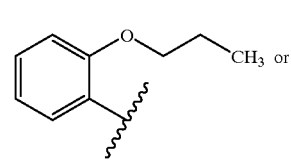

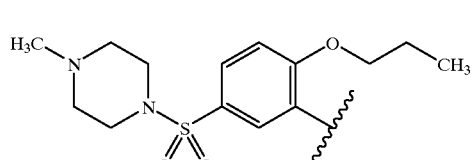

R$_{22}$ is R$_{12}$ or a lower alkyl with the proviso that when R$_{12}$ is a lower alkyl then R$_{11}$ cannot be hydrogen; and R$_8$, R$_{11}$, and R$_{12}$ are as defined above.

Another embodiment of the invention provides compounds having structure IV:

IV
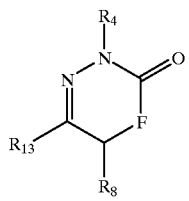
wherein,
F is —CH₂— or sulfur;
R₄ and R₈ are as defined above; and
R₁₃ is:
(i)
(ii)
(iii)
(iv)
(v)
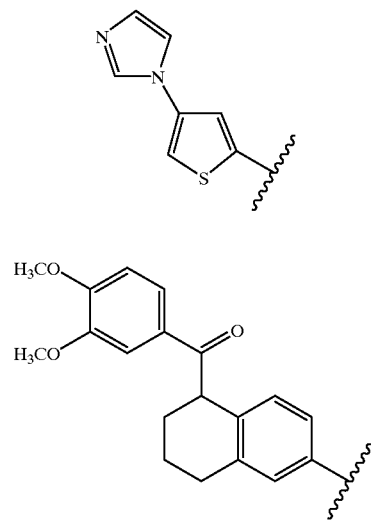
(vi)
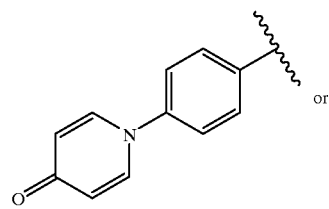
or
(vii)
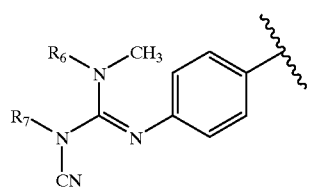
wherein,
R₆ and R₇ are independently hydrogen or R₄, wherein R₄ is as defined above.
Another embodiment of the invention provides compounds having structure V:
V
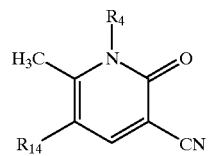
wherein,
R₄ is defined above; and
R₁₄ is:
(i)
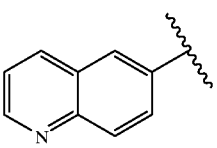
(ii)
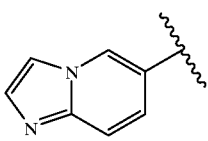
(iii)
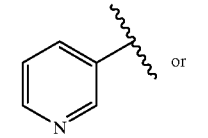
or -continued (iv)

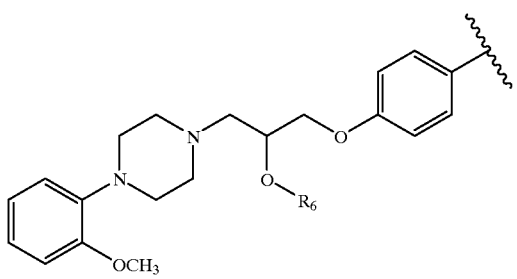

wherein R₆ is as defined above.

Another embodiment of the invention provides compounds having structure VI:

VI

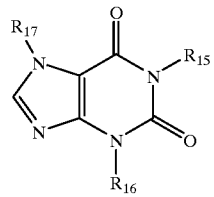

wherein,

R₁₅ is a hydrogen, a lower alkyl, R₄, or —(CH₂)₄—C(CH₃)₂—O—D₁;

R₁₆ is a lower alkyl; and

R₁₇ is a hydrogen, a lower alkyl, CH₃—C(O)—CH₂—; CH₃—O—CH₂—; or D with the proviso that either R₁₅ or R₁₇ must be selected to contain D, wherein D and D₁ are as defined above.

Another embodiment of the invention provides compounds having structure VII:

VII

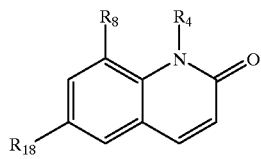

wherein,

R₄ and R₈ are as defined above; and

R₁₈ is:

(i)

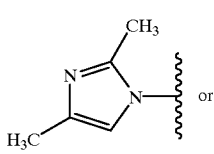

or (ii)

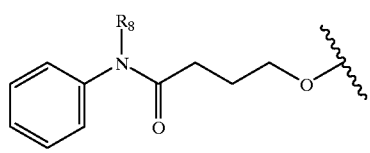

and wherein R₈ is as defined above.

Another embodiment of the invention provides compounds having structure VIII:

VIII

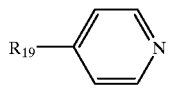

wherein,

R₁₉ is:

(i)

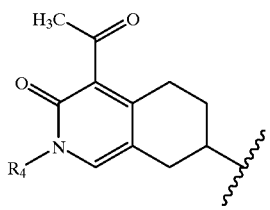

(ii)

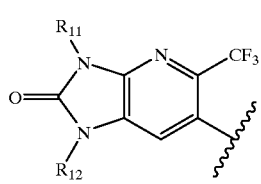

(iii)

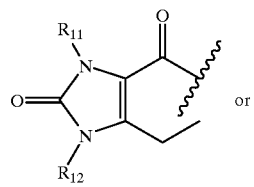

or (iv)

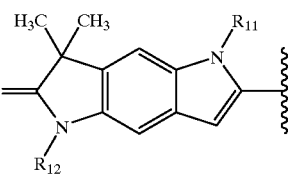

and wherein R₄, R₁₁, and R₁₂ are defined above.

Another embodiment of the invention provides compounds having structure IX:

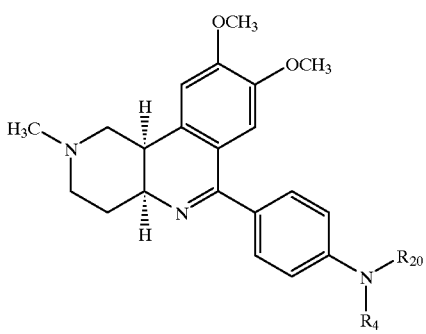

IX wherein $R_{20}$ is:

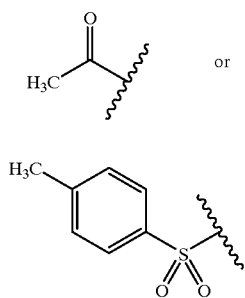

(i)

or (ii)

and wherein $R_4$ is defined above.

Another embodiment of the invention provides compounds having structure X:

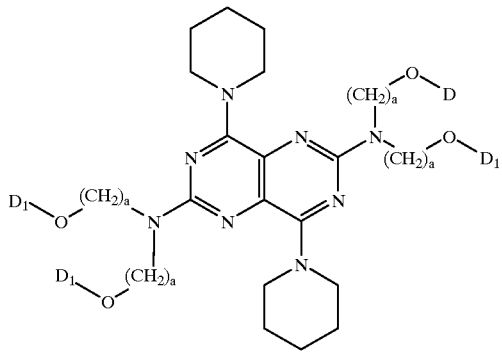

X wherein, a is an integer from 2 to 3 and D and $D_1$ are defined above.

Compounds of the invention which have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the present invention anticipates and includes within its scope all such isomers and mixtures thereof.

Another aspect of the invention provides processes for making the novel compounds of the invention and to the intermediates useful in such processes. Some of the compounds of the invention are synthesized as shown in FIGS. 1–30, in which $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_e$, $R_f$, a, p, D, $D_1$, E, F, G, and X are as defined above or as depicted in the reaction schemes for structures I-X; $P^1$ is an oxygen protecting group and $P^2$ is a sulfur protecting group. The reactions are performed in solvents appropriate to the reagents, and materials used are suitable for the transformations being effected. It will be understood by one skilled in the art of organic synthesis that the functionality present in the molecule must be consistent with the chemical transformation proposed. This will, on occasion, necessitate judgment by the routine as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to the skilled practitioner in the art. The use of sulfur and oxygen protecting groups is well known in the art for protecting thiol and alcohol groups against undesirable reactions during a synthetic procedure and many such protecting groups are known, as described, for example, by T. H. Greene and P. G. M. Wuts, *Protective Groups in Organic Synthesis*, John Wiley & Sons, New York (1991), the disclosure of which is incorporated by reference herein in its entirety.

Another embodiment of this aspect provides processes for making compounds having structure I and to the intermediates useful in such processes as follows.

Nitroso compounds of formula (I) wherein $R_1$, $R_2$, $R_e$, $R_f$, and p are defined above and a nitrite containing imide is representative of the $R_3$ group as defined herein may be prepared as outlined in FIG. 1. The amide group of formula 1 is converted to the imide of formula 2 wherein p, $R_e$ and $R_f$ are defined above by reaction with an appropriate protected alcohol containing activated acylating agent wherein $P^1$ is as defined above. Preferred methods for the formation of imides are reacting the amide with the preformed acid chloride of the protected alcohol containing acid in the presence of pyridine at low temperature or condensing the amide and protected alcohol containing symmetrical anhydride in the presence of a catalyst such as sulfuric acid. Preferred protecting groups for the alcohol moiety are silyl ethers such as a trimethylsilyl ether, a tert-butyldimethylsilyl ether, or a tert-butyldiphenylsilyl ether. Deprotection of the hydroxyl moiety (fluoride ion is, the preferred method for removing silyl ether protecting groups) followed by reaction with a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula IA.

Figure 2:
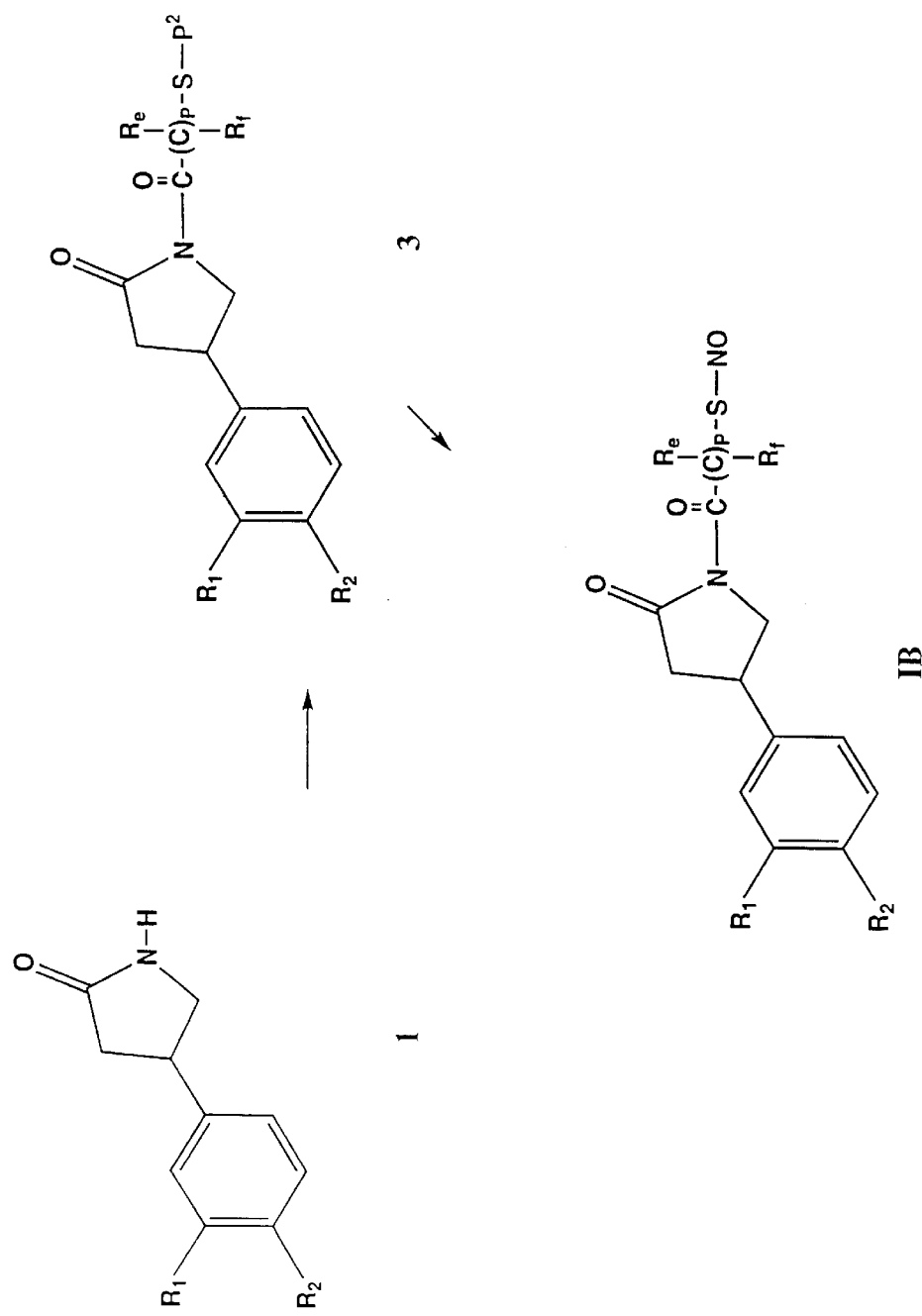
FIG. 2 shows a synthetic scheme for the preparation of nitrosothiol containing substituted benzene derivatives.

Nitroso compounds of formula (I) wherein $R_1$, $R_2$, $R_e$, $R_f$, and p are defined above and a nitrosothiol containing imide is representative of the $R_3$ group as defined herein may be prepared as outlined in FIG. 2. The amide group of formula 1 is converted to the imide of formula 3 wherein p, $R_e$ and $R_f$ are defined herein by reaction with an appropriate protected thiol containing activated acylating agent wherein $P^2$ is as defined herein. Preferred methods for the formation of imides are reacting the amide with the preformed acid chloride of the protected thiol containing acid in the presence of pyridine at low temperature or condensing the amide and protected thiol containing symmetrical anhydride in the presence of a catalyst such as suifriric acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically used to hydrolyze thioesters and Nmethoxymethyl thiocarbamates and mercuric trifluoroacetate, silver nitrate, or strong acids such as trifluoroacetic or hydrochloric acid and heat are used to remove a paramethoxyberizyl thi oether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula IB. Alternatively, treatment of the deprotected thiol derived from compound 3 with a stoichiometric quantity of sodium nitrite in an acidic aqueous or alcoholic solution affords the compound of the formula IB.

Figure 3:
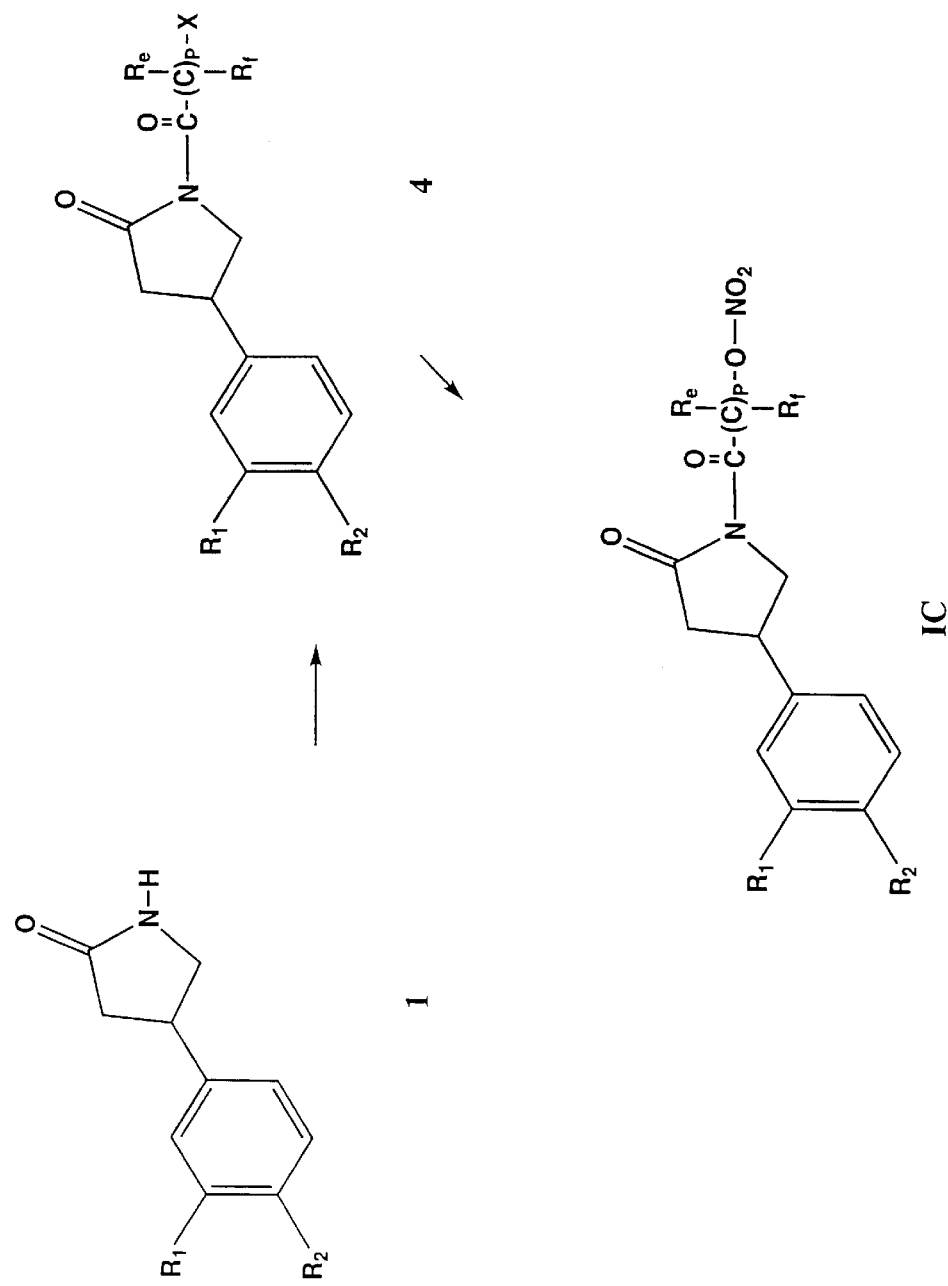
FIG. 3 shows a synthetic scheme for the preparation of nitrate containing substituted benzene derivatives.

Nitro compounds of formula (1) wherein $R_1$, $R_2$, $R_e$, $R_f$, and p are defined herein and a nitrate containing imide is representative of the $R_3$ group as defined herein may be prepared as outlined in FIG. 3. The amide group of the formula 1 is converted to the imide of the formula 4 wherein p, $R_e$ and $R_f$ are defined above and X is a halogen by reaction with an appropriate halide containing activated acylating agent. Preferred methods for the formation of imides are reacting the amide with the preformed acid chloride of the halide containing acid in the presence of pyridine at low temperature or condensing the amide and halide containing symmetrical anhydride in the presence of a catalyst such as suifriric acid. Preferred halides are bromide and iodide. Reaction of the imide of the formula 4 with a suitable penetrating agent such as silver nitrate in an inert solvent such as acetonitrile affords the compound of the formula IC.

Another embodiment of this aspect provides processes for making compounds having structure II and to the intermediates useful in such processes as follows.

Figure 4:
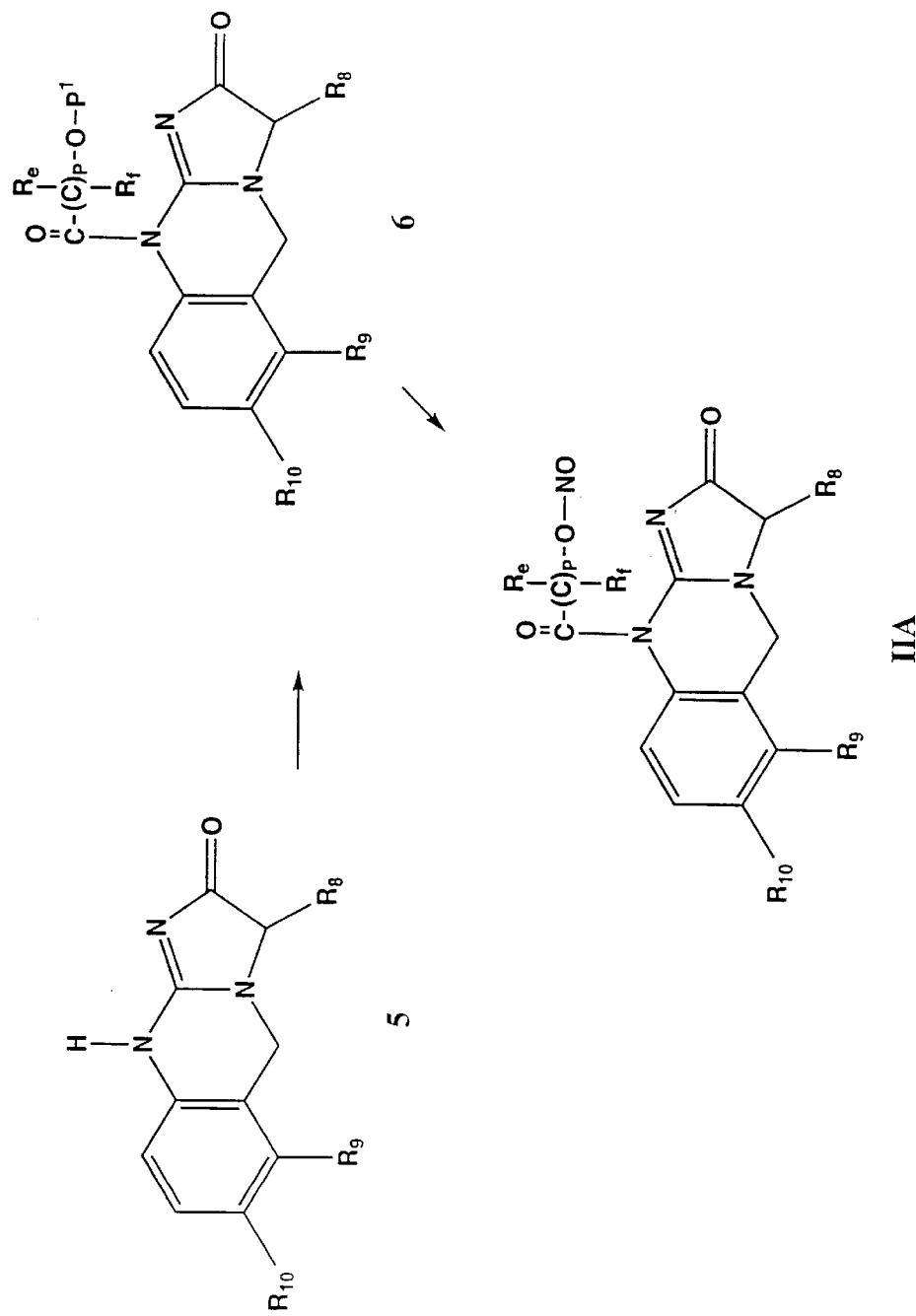
FIG. 4 shows a synthetic scheme for the preparation of nitrite containing imidazo[2,1-b]quinazoline derivatives.

Nitroso compounds of formula (II) wherein R, $R_9$, $R_{10}$, $R_e$, $R_f$, and p are defined above and a nitrite containing amide is representative of the $R_4$ group as defined above may be prepared as outlined in FIG. 4. The imidazo[2,1-b]quinazoline of formula 5 is converted to the acylimidazo[2,1-b]quinazoline of formula 6 wherein p, $R_e$ and $R_f$ are defined above by reaction with an appropriate protected alcohol containing activated acylating agent wherein $P^1$ is as defined above. Preferred methods for the formation of acylimidazo[2,1-b]quinazolines are reacting the imidazo[2,1-b]quinazoline with the preformed acid chloride or symmetrical anhydride of the protected alcohol containing acid or condensing the imidazo[2,1-b]quinazoline and protected alcohol containing acid in the presence of a dehydrating agent such as dicyclohexylcarbodiimide (DCC) or 1-ethyl-3-(3-dimethylaminopropyl) carbodiimicle hydrochloride (EDAC HCl) with or without a catalyst such as 4dimethylamino-pyridine (DMAP) or 1-hydroxybenzotriazole (HOBt). Preferred protecting groups for the alcohol moiety are silyl ethers such as a trimethylsilyl or tertbutyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula IIA.

Figure 5:
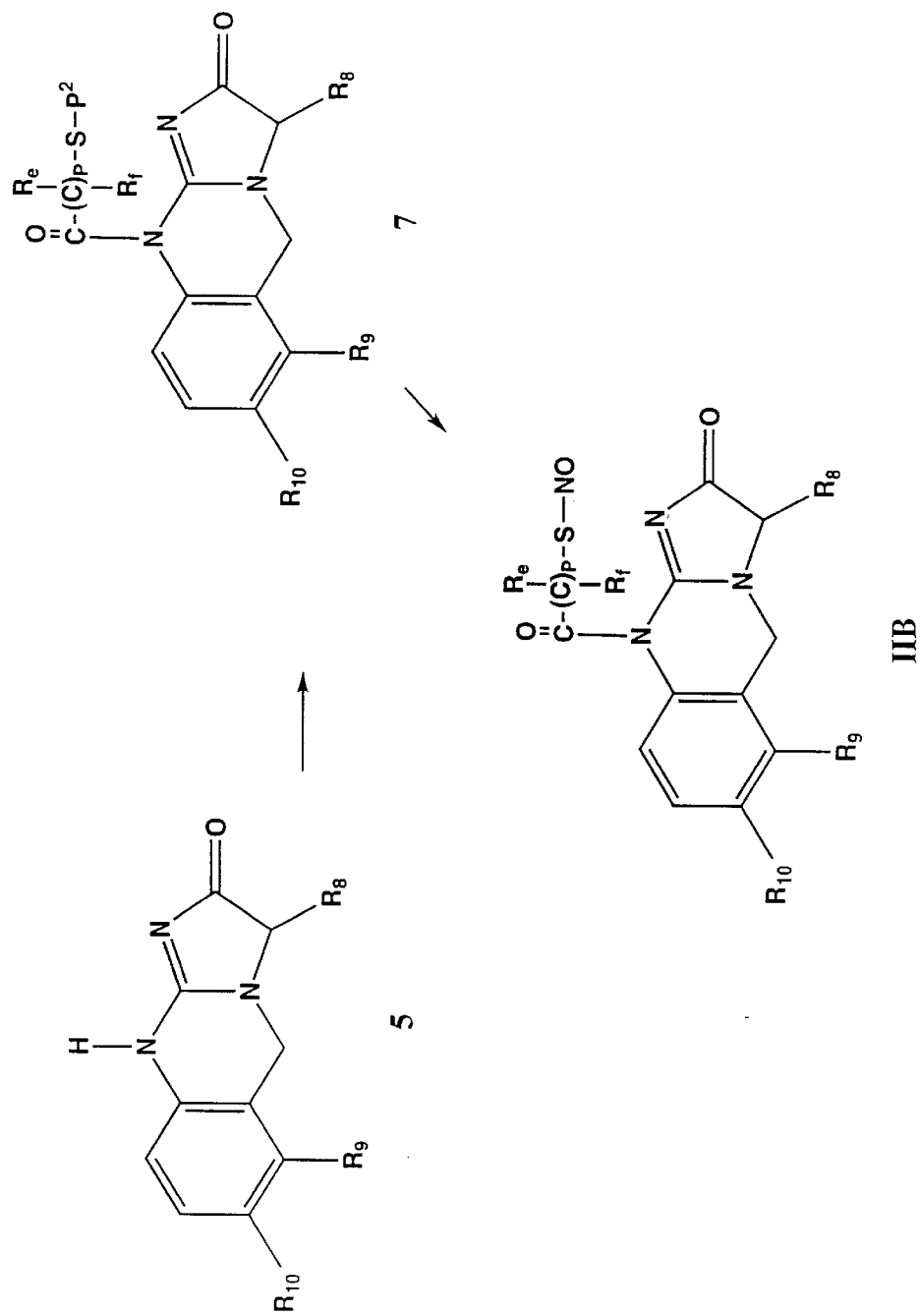
FIG. 5 shows a synthetic scheme for the preparation of nitrosothiol containing imidazo[2,1-b]quinazoline derivatives.

Nitroso compounds of formula (II) wherein $R_8$, $R_9$, $R_{10}$, $R_e$, $R_f$, and p are defined above and a nitrosothiol containing amide is representative of the $R_4$ group as defined above on may be prepared as outlined in FIG. 5. The imidazo[2,1-b]quinazoline of formula 5 is converted to the acylimidazo[2,1-b]quinazoline of formula 7 wherein p, $R_e$ and $R_f$ are defined above by reaction with an appropriate protected thiol containing activated acylating agent wherein P is as defined above. Preferred methods for the formation of acylated imidazo[2,1-b]quinazolines are reacting the imidazo[2,1-b]quinazoline with the preformed acid chloride or symmetrical anhydride of the protected thiol containing acid or condensing the imidazo[2,1-b]quinazoline and protected thiol containing acid in the presence of a dehydrating agent such as DCC or EDAC HCl with or without a catalyst such as DMAP or HOBt. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenyiphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula IIB. Alternatively, treatment of the deprotected thiol derived from compound 7 with a stoichiometric quantity of sodium nitrite in an acidic aqueous or alcoholic solution affords the compound of the formula IIB.

Figure 6:
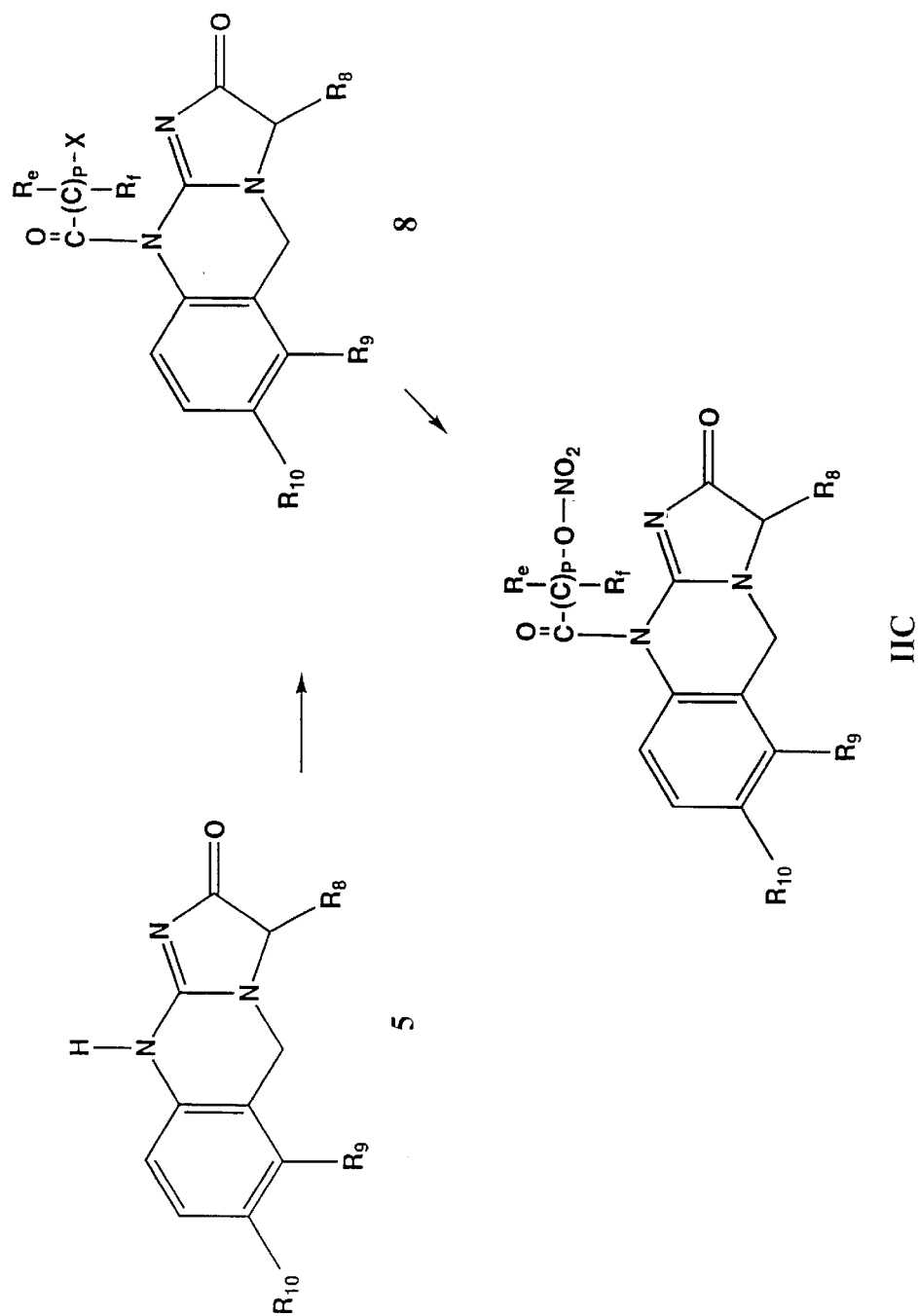
FIG. 6 shows a synthetic scheme for the preparation of nitrate containing imidazo[2,1-b]quinazoline derivatives.

Nitro compounds of formula (II) wherein $R_8$, $R_9$, $R_{10}$, $R_e$, $R_f$, and p are defined above and a nitrate containing amide is representative of the $R_4$ group as defined above may be prepared as outlined in FIG. 6. The imidazo[2,1-b]quinazoline of formula 5 is converted to the acylimidazo[2,1-b]quinazoline of formula 8 wherein p, $R_e$ and $R_f$ are defined above and X is a halogen by reaction with an appropriate halide containing activated acylating agent. Preferred methods for the formation of the acylimidazo[2,1-b]quinazolines are reacting the imidazo[2,1-b]quinazoline with the preformed acid chloride or symmetrical anhydride of the halide containing acid or condensing the alcohol and halide containing acid in the presence of a dehydrating agent such as DCC or EDAC HCl with or without a catalyst such as DMAP or HClBt. Preferred halides are bromide and iodide. Reaction of the acylimidazo[2,1-b]quinazoline of the formula 8 with a suitable nitrating agent such as silver nitrate in an inert solvent such as acetonitrile affords the compound of the formula IIC.

Another embodiment of this aspect provides processes for making compounds having structure III and to the intermediates useful in such processes as follows.

Figure 7:
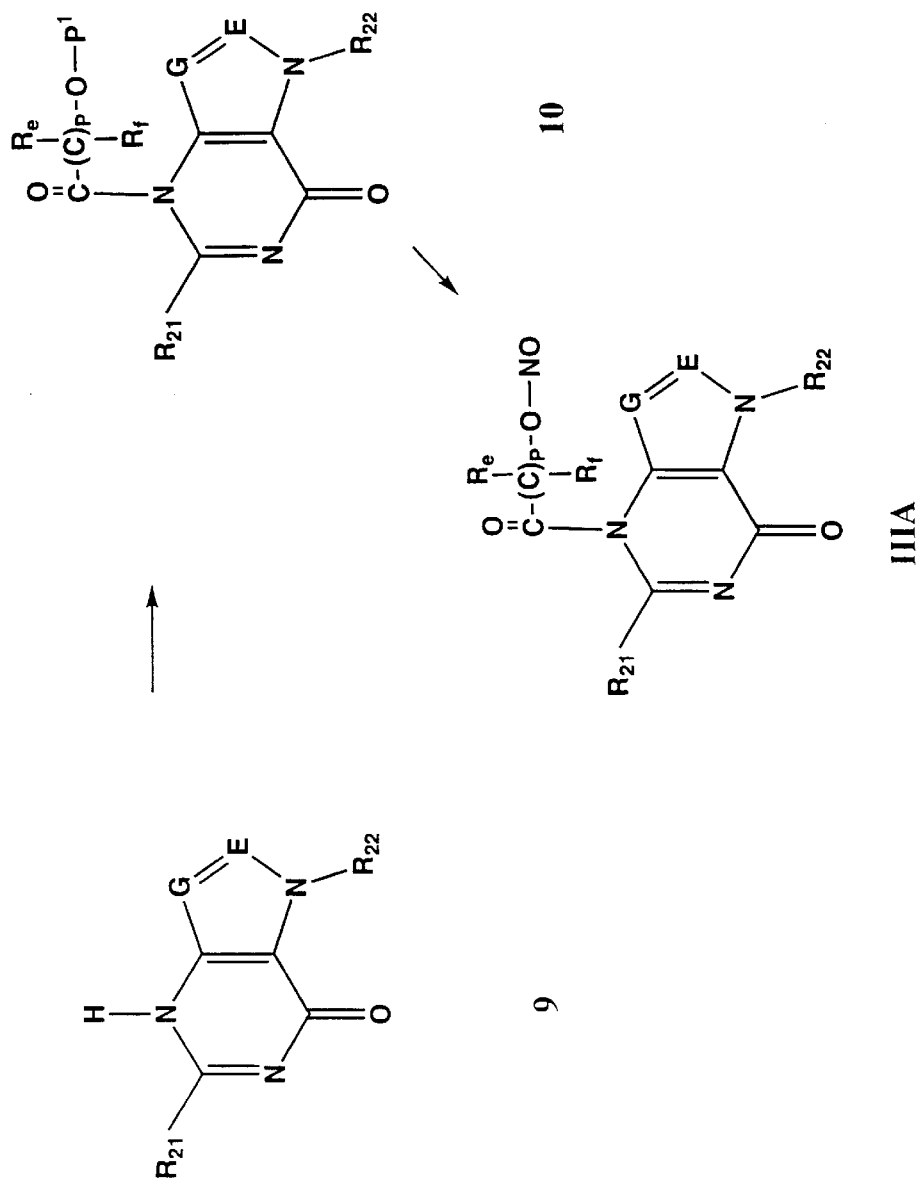
FIG. 7 shows a synthetic scheme for the preparation of nitrite containing purine-6-one derivatives.

Nitroso compounds of formula (III) wherein E, M, $R_{21}$, $R_{22}$, $R_e$, $R_f$, and p are defined above and a nitrite containing amide is representative of the $R_{11}$ group as defined in this specification may be prepared as outlined in FIG. 7. The purine-6-one group of formula 9 is converted to the acylated purine-6-one of formula 10 wherein. p, $R_e$ and $R_f$ are defined above by reaction with an appropriate protected alcohol containing activated acylating agent wherein $P^1$ is as defined in this specification. Preferred methods for the formation of acylated purine-6-ones are reacting the purine-6-one with the preformed acid chloride or symmetrical anhydride of the protected alcohol containing acid. Preferred protecting groups for the alcohol moiety are silyl ethers such as a tert-butyldimethylsilyl ether or a tert-butyldiphenylsilyl ether. Deprotection of the hydroxyl moiety (fluoride ion is the preferred method for removing silyl ether protecting groups) followed by reaction a suitable nitrosylating agent such as thionyl chloride nitrite, thionyl di nitrite, or nitrosonium tetrafluoroborate in a suitable anhydrous solvent such as dichloromethane, THF, DMF, or acetonitrile with or without an amine base such as pyridine or triethylamine affords the compound of the formula IIIA.

Figure 8:
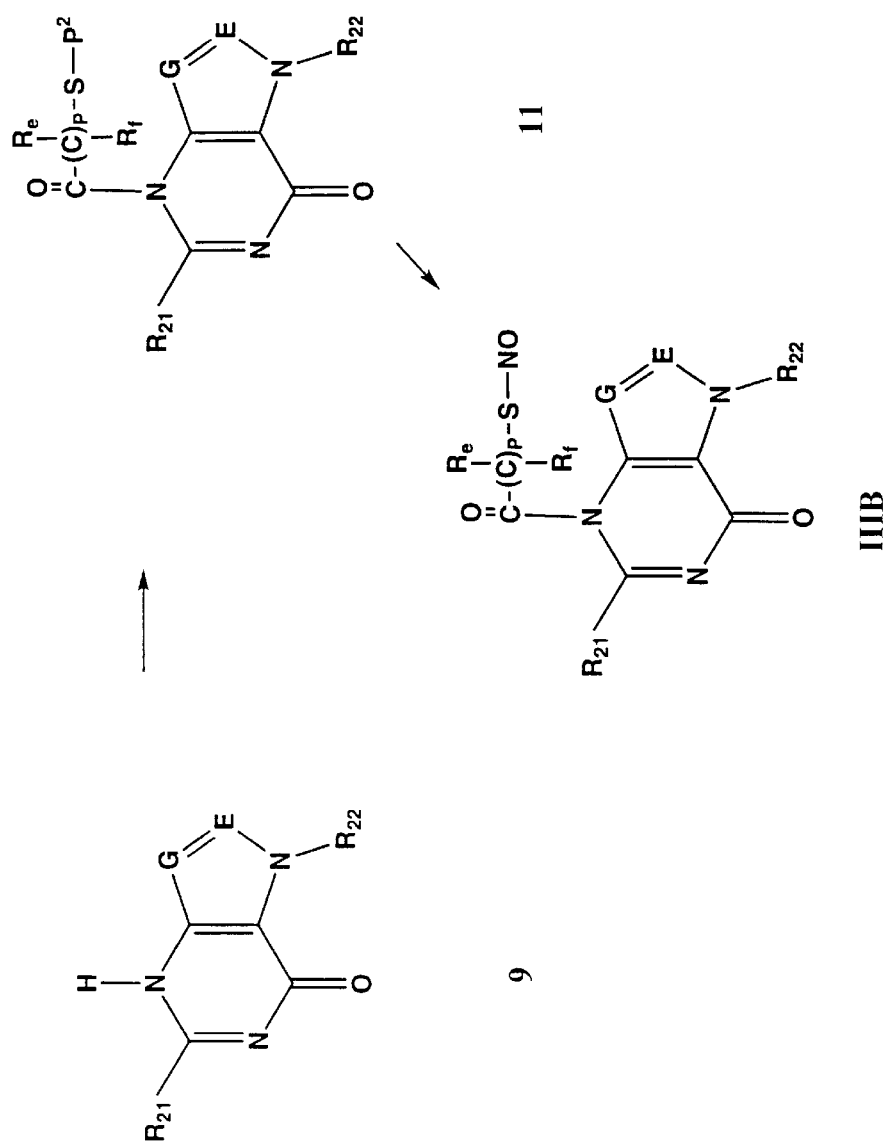
FIG. 8 shows a synthetic scheme for the preparation of nitrosothiol containing purine-6-one derivatives.

Nitroso compounds of formula (III) wherein E, M, $R_{21}$, $R_{22}$, $R_e$, $R_f$, and p are defined above and an nitrosothiol containing amide is representative of the $R_{11}$ group as defined above may be prepared as outlined in FIG. 8. The purine-6-one group of formula 9 is converted to the acylated purine6-one of formula 11 wherein p, $R_e$ and $R_f$ are defined above by reaction with an appropriate protected thiol containing activated acylating agent wherein $P^2$ is as defined above. Preferred methods for the formation of acylated purine-6-ones are reacting the purine-6-one with the preformed acid chloride or symmetrical anhydride of the protected alcohol containing acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxyberzyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula IIIB. Alternatively, treatment of the deprotected thiol derived from compound 11 with a stoichiometric quantity of sodium nitrite in an acidic aqueous or alcoholic solution affords the compound of the formula IIIB.

Figure 9:
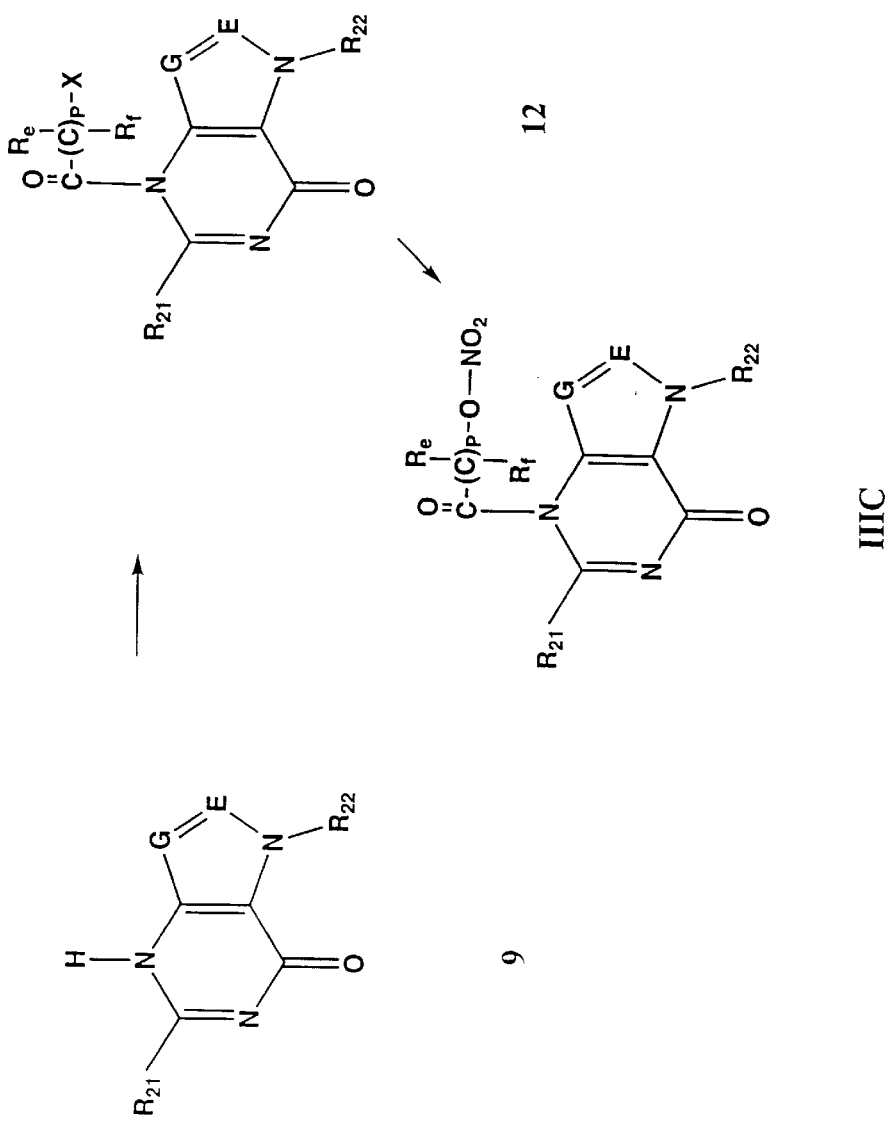
FIG. 9 shows a synthetic scheme for the preparation of nitrate containing purine-6-one derivatives.

Nitro compounds of formula (III) wherein E, M, $R_{21}$, $R_{22}$, $R_e$, $R_f$, and p are defined above and an nitrate containing amide is representative of the $R_{11}$ group as, defined above may be prepared as outlined in FIG. 9. The purine-6-one of formula 9 is converted to the acylated purine-6-one of formula 12 wherein p, $R_e$ and $R_f$ are defined above and X is halogen. Preferred methods for the formation of acylated purine-6-ones are reacting the purine-6-one with the preformed acid chloride or symmetrical anhydride of the halide containing acid. Preferred halides are bromide and iodide. Reaction of the of the acylated purine-6-one of the formula 12 with a suitable nitrating agent such as silver nitrate in an inert solvent such as acetonitrile affords the compound of the formula IIIC.

Another embodiment of this aspect provides processes for making compounds having structure IV and to the intermediates useful in such processes as follows.

Figure 10:
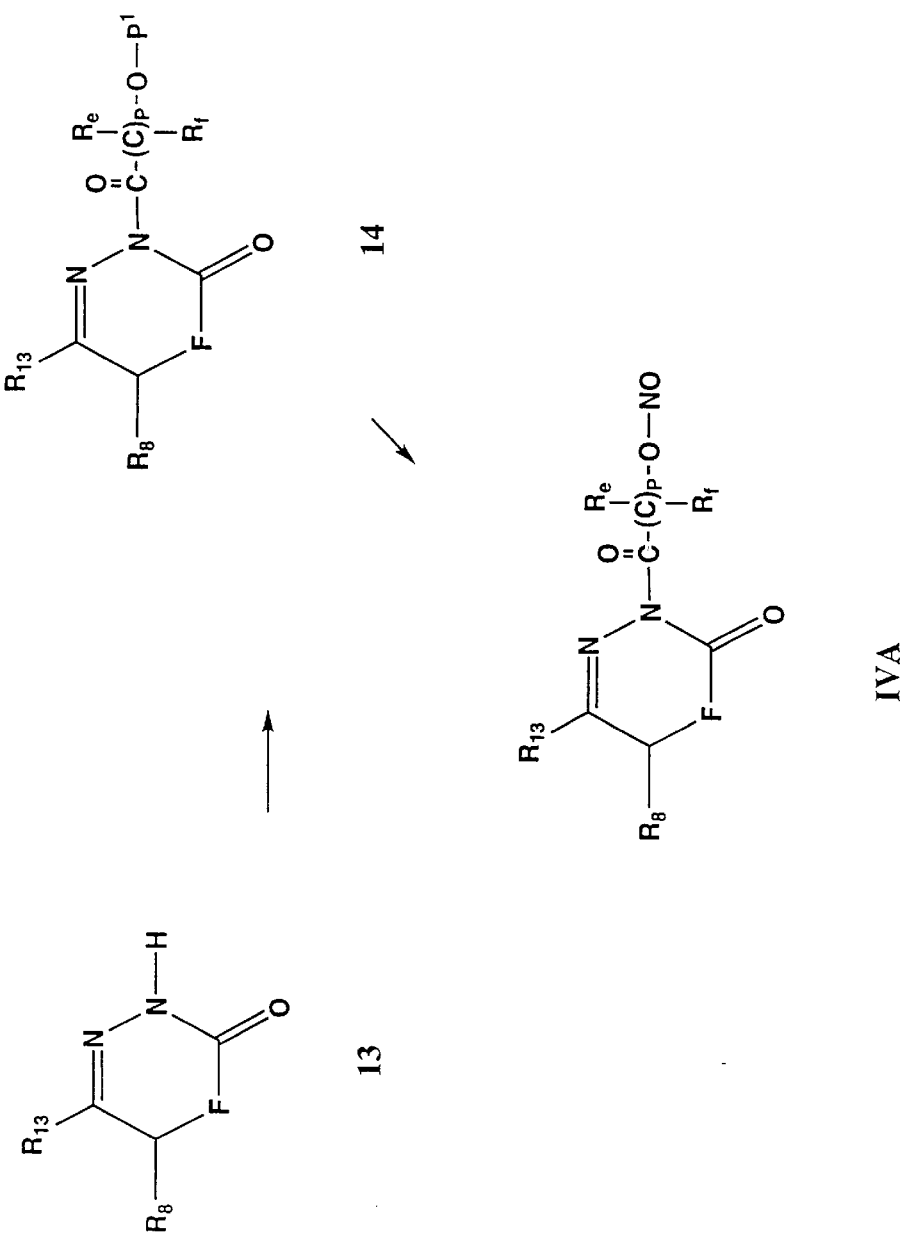
FIG. 10 shows a synthetic scheme for the preparation of nitrite containing pyrimidin-4-one derivatives.

Nitroso compounds of formula (IV) wherein F, $R_8$ $R_{13}$, $R_e$, $R_f$, and p are defined above and a nitrite containing acyl hydrazide is representative of the $R_4$ group as defined above may be prepared as outlined in FIG. 10. The 3 (2-H)-pyridazinone or 2H-1,2,3,4-thiadiazine of formula 13 is converted to the 3 (2-acyl)-pyridazinone or 2-acyl-1,2,3,4-thiadiazine of formula 14 wherein p, $R_e$ and $R_f$ are defined above by reaction with an appropriate protected alcohol containing activated acylating agent wherein $P^1$ is defined above. Preferred methods for the formation of 3 (2-acyl)-pyridazinone or 2-acyl-1,2,3,4-thiadiazine are reacting the 3 (2H)-pyridazinone or 2-H-1,2,3,4-thiadiazine with the preformed acid chloride or symmetrical anhydride of the protected alcohol containing acid or condensing the 3 (2-H)-pyridazinone or 2H-1,2,3,4-thiadiazine and protected alcohol containing acid in the presence of a dehydrating agent such as DCC or EDAC HCl with a catalyst such as DMAP or HOBt. Preferred protecting groups for the alcohol moiety are silyl ethers such as a tert-butyldimethylsilyl ether or a tert-butyldiphenylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula IVA.

Figure 11:
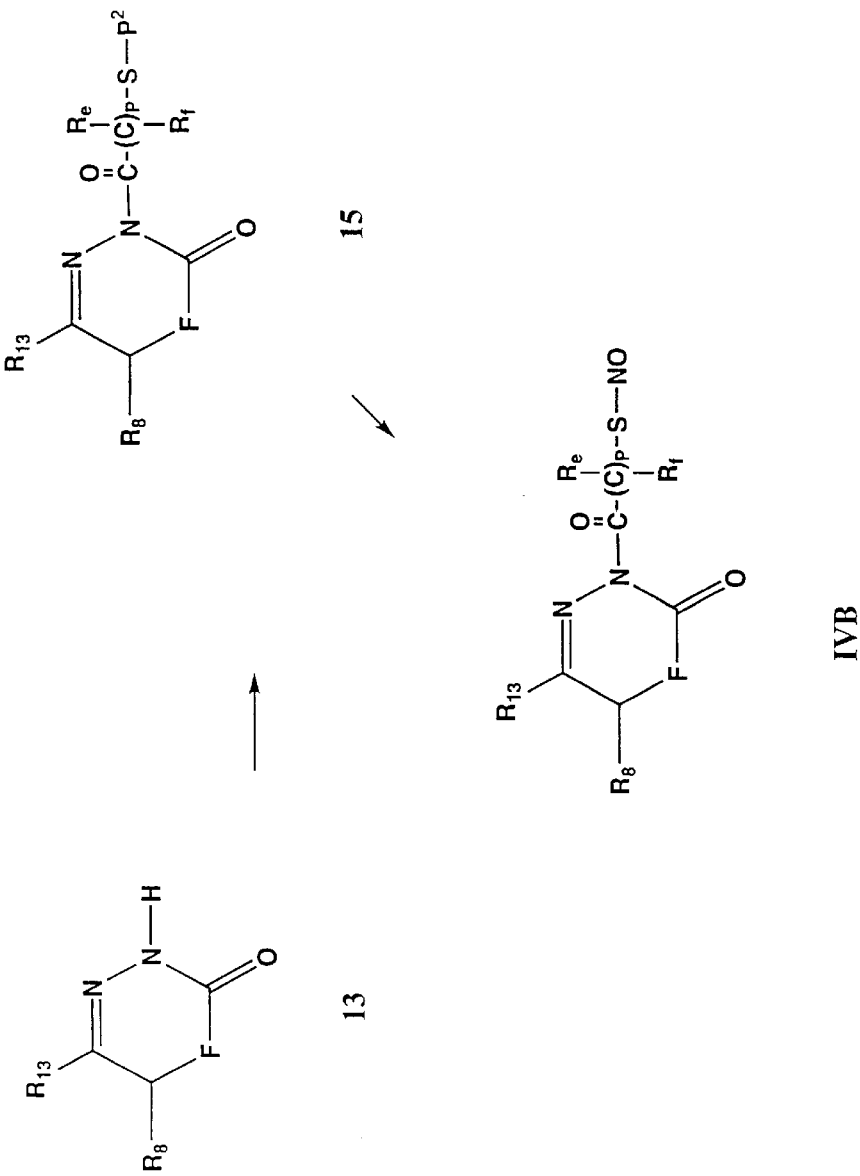
FIG. 11 shows a synthetic scheme for the preparation of nitrosothiol containing pyrimidin-4-one derivatives.

Nitroso compounds of formula (IV) wherein F, $R_8$, $R_{13}$, $R_e$, $R_f$, and p are defined above and a nitrosothiol containing acyl hydrazide is representative of the $R_4$ group as defined above may be prepared as outlined in FIG. 11. The 3 (2-H)-pyridazinone or 2H-1,2,3,4-thiadiazine of formula 13 is converted to the 3 (2-acyl)-pyridazinone or 2-acyl-1,2,3, 4thiadiazine of formula 15 wherein p, $R_e$ and $R_f$ are defined above by reaction with an appropriate protected thiol containing activated acylating agent wherein $P^2$ is as defined above. Preferred methods for the formation of3 (2-acyl)-pyridazinones or 2-acyl-1,2,3,4-thiadiazines are reacting the 3 (2-H)-pyridazinone or 2H-1,2,3,4-thiadiazine with the preformed acid chloride or symmetrical, anhydride of the protected thiol containing acid or condensing the 3 (2-H)-pyridazinone or 2H-1,2,3,4-thiadiazine and protected thiol containing acid in the presence of a dehydrating agent such as DCC or EDAC HCl with a catalyst such as DMAP or HOBt. Preferred protecting groups for the thiol moiety are as a thioester such as a thioacetate or thiobenzoate, as a disulfide, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula IVB. Alternatively, treatment of the deprotected thiol derived from compound 15 with a stoichiometric quantity of sodium nitrite in an acidic aqueous or alcoholic solution affords the compound of the formula IVB.

Figure 12:
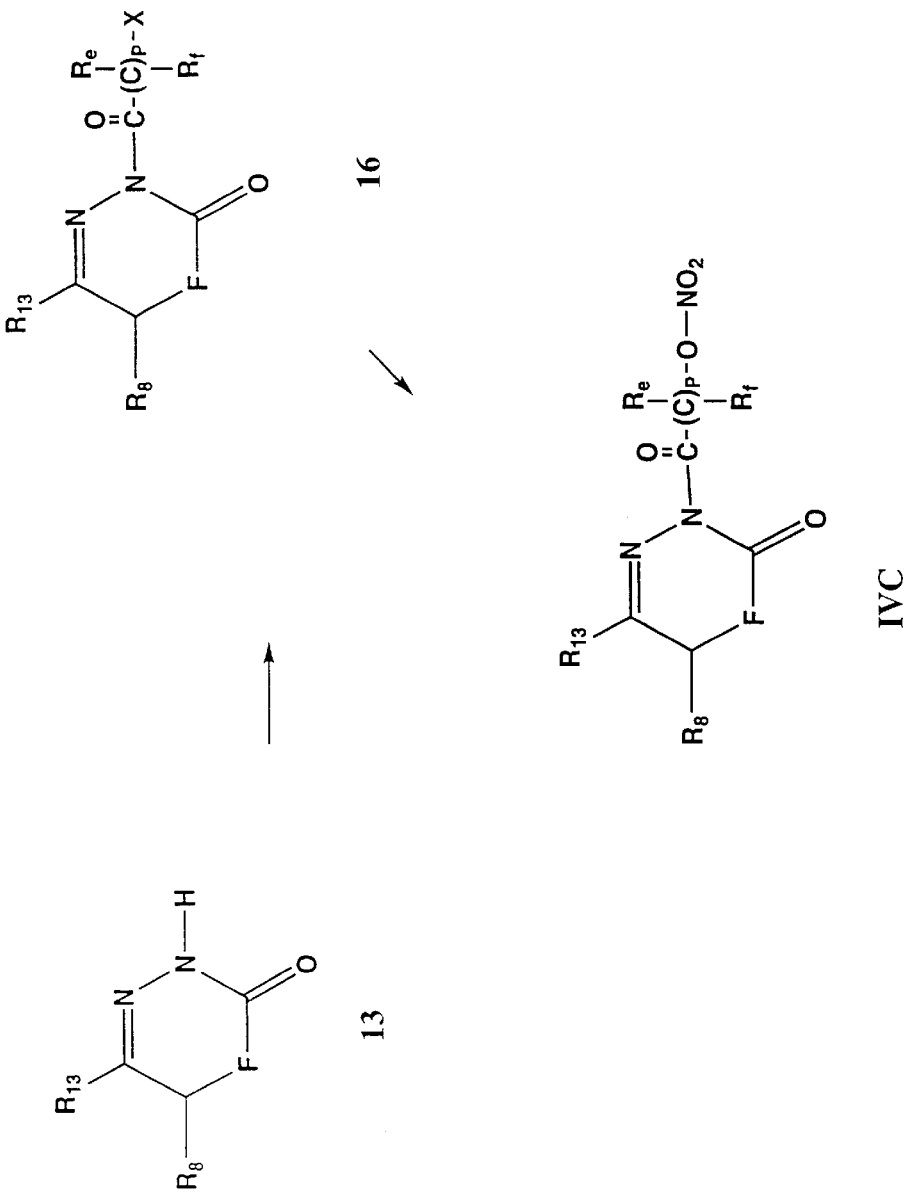
FIG. 12 shows a synthetic scheme for the preparation of nitrate containing pyrimidin-4-one derivatives.

Nitro compounds of formula (IV) wherein F, $R_8$ $R_{13}$, $R_e$, $R_f$, and p are defined above and an nitrate containing acyl hydrazide is representative of the $R_4$ group as defined above may be prepared as outlined in FIG. 12. The 3 (2-H)-pyridazinone or 2H-1,2,3,4-thiadiazine of formula 13 is converted to the 3 (2-acyl)-pyridazinone or 2-acyl-1,2,3,4-thiadiazine of formula 16 wherein p, $R_e$ and $R_f$ are defined above and X is halogen. Preferred methods for the formation of 3 (2-acyl)-pyridazinones or 2-acyl-1,2,3,4-thiadiazines are reacting the 3 (2-H)-pyridazinone or 2H-1,2,3,4-thiadiazine with the preformed acid chloride or symmetrical anhydride of the halide containing acid or condensing the 3 (2-H)-pyridazinone or 2H-1,2,3,4-thiadiazine and halide containing acid in the presence of a dehydrating agent such as DCC or EDAC HCl with a catalyst such as DMAP or HOBt. Preferred halides are bromide and iodide. Reaction of the 3 (2-acyl)-pyridazinone or 2-acyl-1,2,3,4-thiadiazine of formula 16 with a suitable nitrating agent such as silver nitrate in an inert solvent such as acetonitrile affords the compound of the formula IVC.

Another embodiment of this aspect provides processes for making compounds having structure V and to the intermediates useful in such processes as follows.

Figure 13:
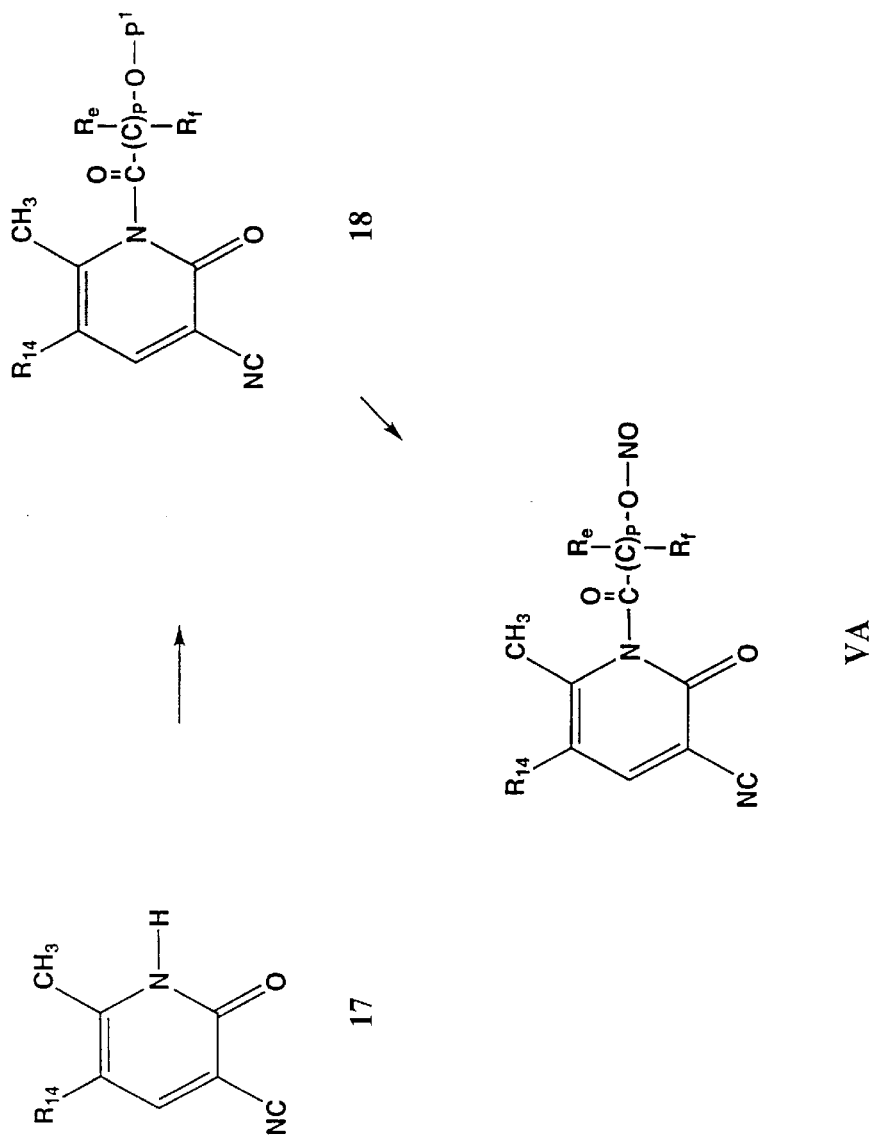
FIG. 13 shows a synthetic scheme for the preparation of nitrite containing 2-pyridone derivatives.

Nitroso compounds of formula (V) wherein $R_{14}$, $R_e$, $R_f$, and p are defined above and an nitrite containing imide is representative of the $R_4$ group as defined above may be prepared as outlined in FIG. 13. The amide group of formula 17 is converted to the imide of formula 18 wherein p, $R_e$, and $R_f$ are defined as in this specification by reaction with an appropriate protected alcohol containing activated acylating agent wherein $P^1$ is as defined in this specification. Preferred methods for the formation of imides are reacting the amide with the preformed acid chloride of the protected alcohol containing acid in the presence of pyridine at low temperature or condensing the amide and protected alcohol containing symmetrical anhydride in the presence of a catalyst such as sulfuric acid. Preferred protecting groups for the alcohol moiety are silyl ethers such as a tert-butyldimethylsilyl ether or a tert-butyldiphenylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as; pyridine or triethylamine affords the compound of the formula VA.

Figure 14:
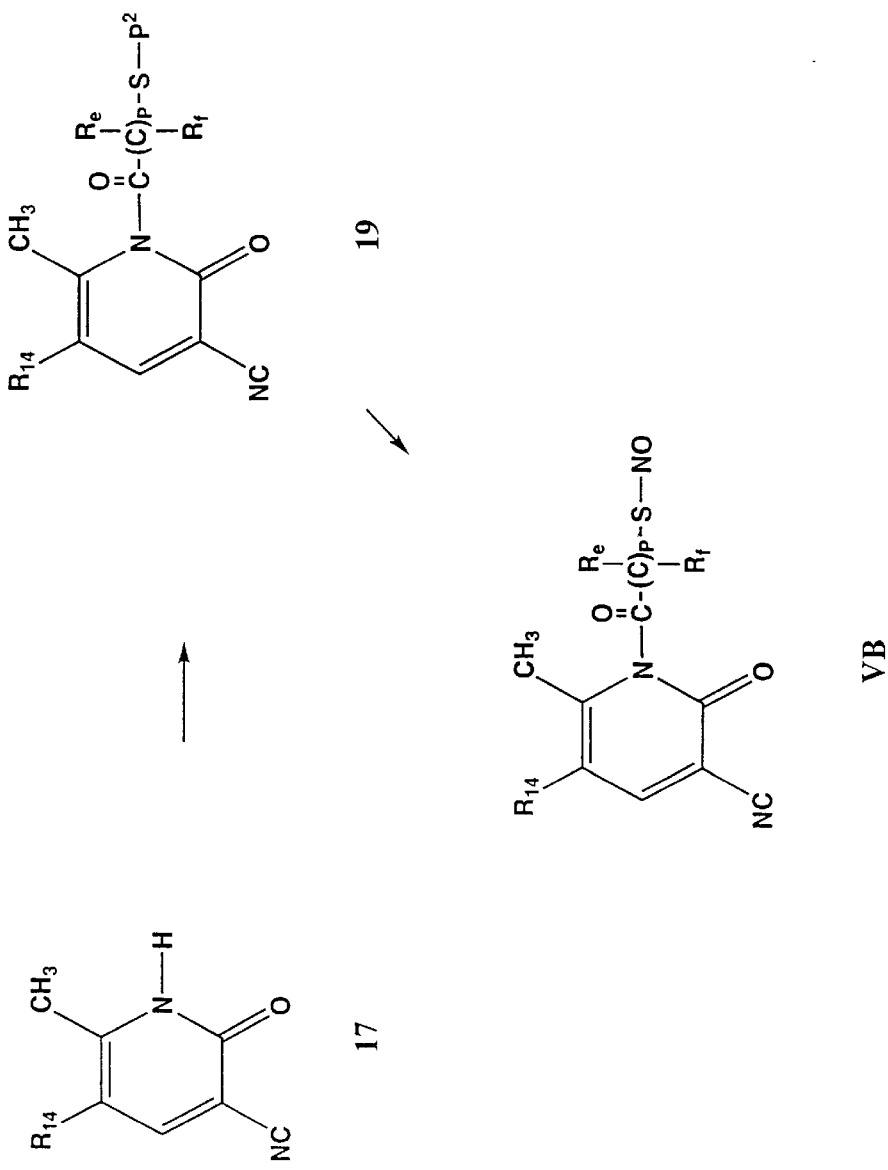
FIG. 14 shows a synthetic scheme for the preparation of nitrosothiol containing 2-pyridone derivatives.

Nitroso compounds of formula (V) wherein $R_{14}$, $R_e$, $R_f$, and p are defined above and a nitrosothiol containing imide is representative of the $R_4$ group as defined above may be prepared as outlined in FIG. 14. The amide group of formula 17 is converted to the imide of formula 19 wherein p, $R_e$ and $R_f$ are defined above by reaction with an appropriate protected thiol containing activated acylating agent wherein $P^2$ is as defined above. Preferred methods for the formation of imides are reacting the amide with the preformed acid chloride of the protected thiol containing acid in the presence of pyridine at low temperature or condensing the amide and protected thiol containing symmetrical anhydride in the presence of a catalyst such as sulfuric acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically used to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula VB. Alternatively, treatment of the deprotected thiol derived from compound 19 with a stoichiometric quantity of sodium nitrite in an acidic aqueous or alcoholic solution affords the compound of the formula VB.

Figure 15:
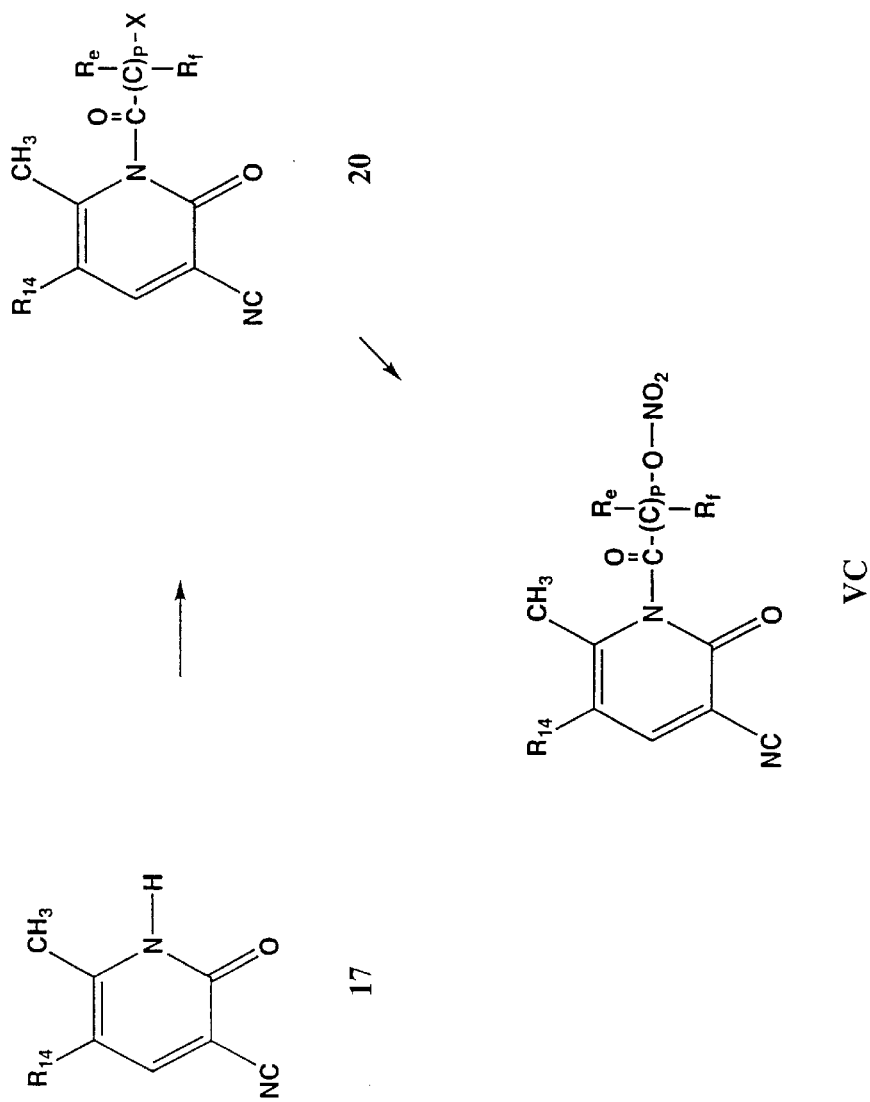
FIG. 15 shows a synthetic scheme for the preparation of nitrate containing 2-pyridone derivatives.

Nitro compounds of formula (V) wherein $R_{14}$, $R_e$, $R_f$, and p are defined above and a nitrate containing imide is representative of the $R_4$ group as defined above may be prepared as outlined in FIG. 15. The amide group of the formula 17 is converted to the imide of the formula 20 wherein p, $R_e$ and $R_f$ are defined above and X is a halogen by reaction with an appropriate halide containing activated acylating agent. Preferred methods for the formation of imides are reacting the amide with the preformed acid chloride of the halide containing acid in the presence of pyridine at low temperature or condensing the amide and halide containing symmetrical anhydride in the presence of a catalyst such as sulfuric acid. Preferred halides are bromide and iodide. Reaction of the imide of the formula 20 with a suitable nitrating agent such as silver nitrate in an inert solvent such as acetonitrile affords the compound of the formula VC.

Another embodiment of this aspect provides processes for making compounds having structure VI and to the intermediates useful in such processes as follows.

Figure 16:
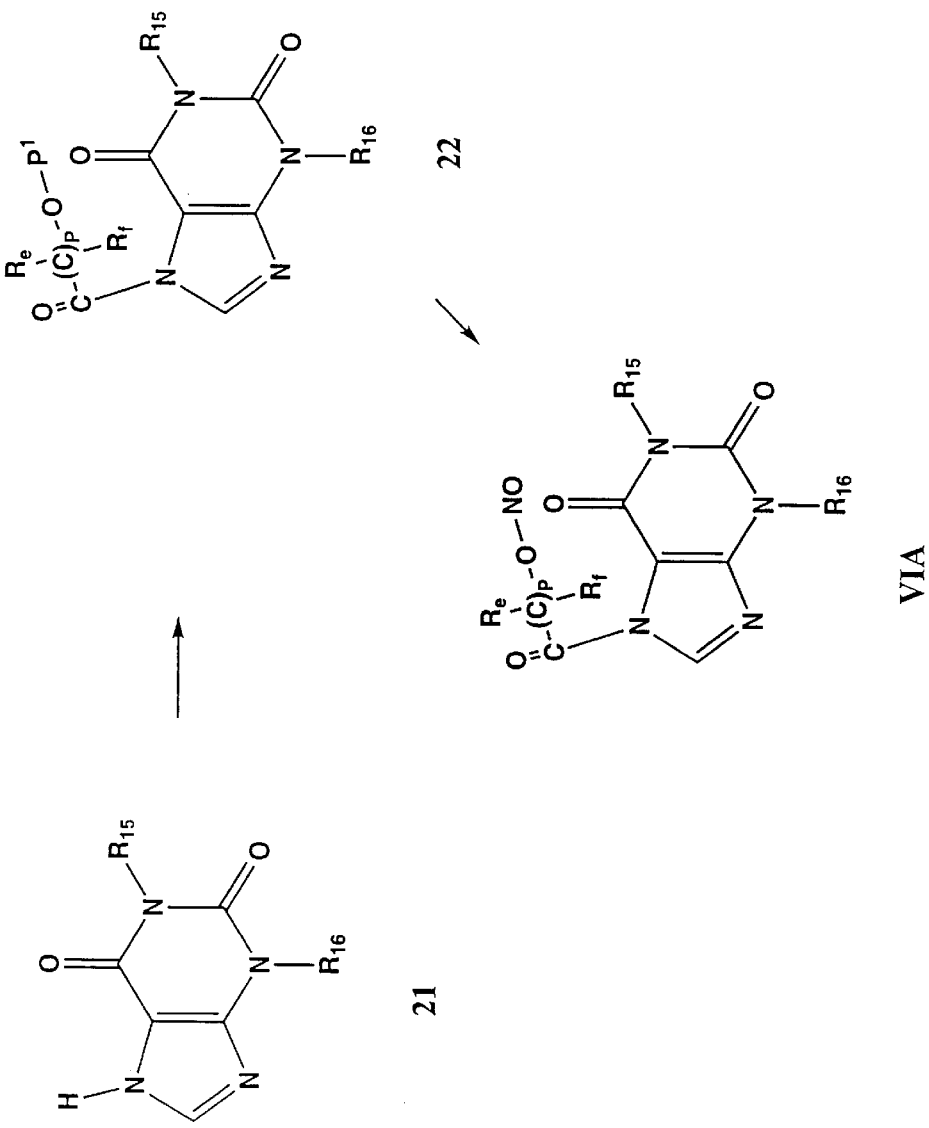
FIG. 16 shows a synthetic scheme for the preparation of nitrite containing purine-2,6-dione derivatives.

Nitroso compounds of formula (VI) wherein $R_{15}$, $R_{16}$, $R_e$, $R_f$ and p are defined above and a nitrite containing acyl imidazolide is representative of the $R_{17}$ group as defined above may be prepared as outlined in FIG. 16. The 1H-purine-2,6-dione of formula 21 is converted to the acylated derivative of the formula 22 wherein p, $R_e$ and $R_f$ are defined above by reaction with an appropriate protected alcohol containing activated acylating agent wherein $P_1$ is defined above. Preferred methods for the formation of acylated 1H-purine-2,6-diones are reacting the 1H-purine-2,6-dione with the preformed acid chloride or symmetrical anhydride of the protected alcohol containing acid or condensing the 1H-purine-2,6-dione and protected alcohol containing acid in the presence of a dehydrating agent such as DCC or EDAC HCl with a catalyst such as DMAP or HOBt. Preferred protecting groups for the alcohol moiety are silyl ethers such as a tert-butyldimethylsilyl ether or a tert-butyldimethyl-silyl ether. Deprotection of the hydroxyl moiety (fluoride ion is the preferred method for removing silyl ether protecting groups) followed by reaction a suitable nitroslating agent such as thionyl chloride nitrite, thionyl dinitrite, or nitrosonium tetrafluoroborate in a suitable anhydrous solvent such as dichloromethane THF, DMF, or acetonitrile with or without an amine base such as pyridine or triethylamine affords the compound of the formula VIA.

Figure 17:
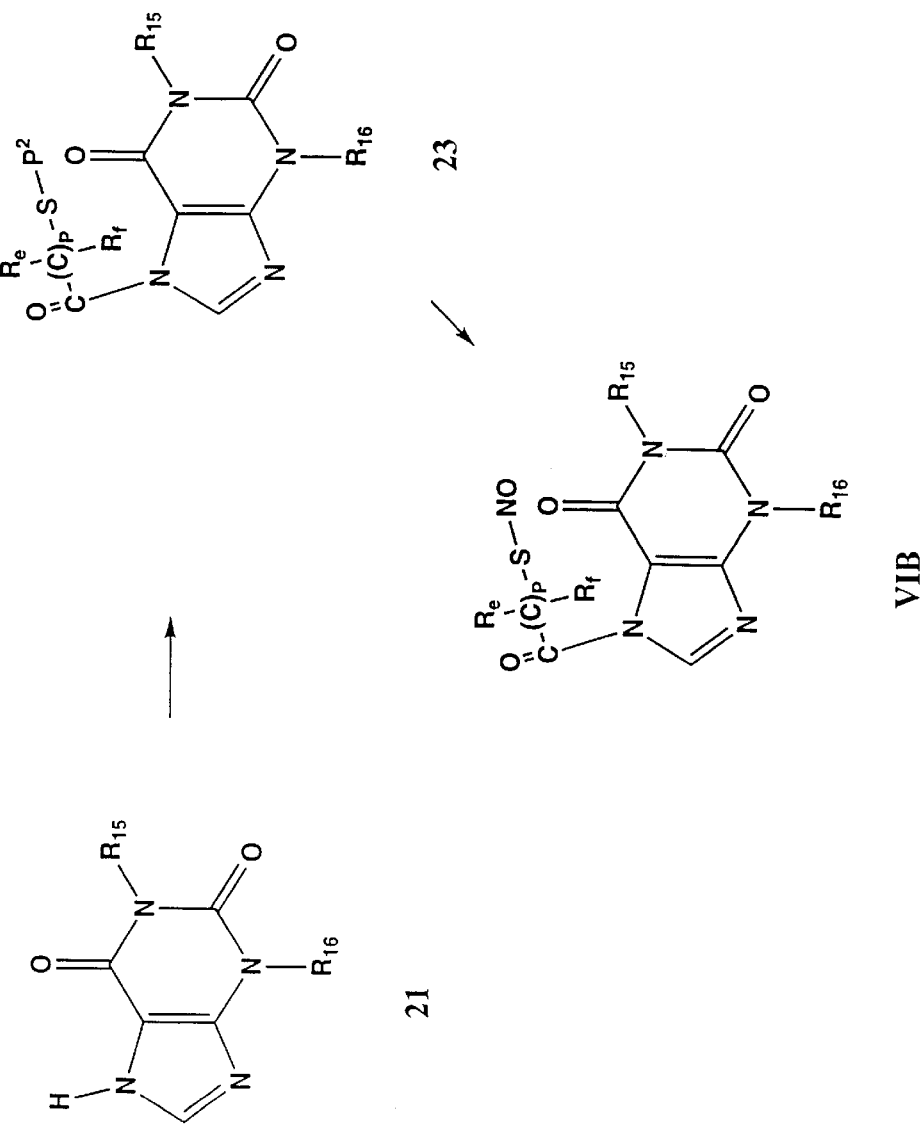
FIG. 17 shows a synthetic scheme for the preparation of nitrosothiol containing purine-2,6-dione derivatives.

Nitroso compounds of formula (VI) wherein $R_{15}$, $R_{16}$, $R_e$, $R_f$, and p are defined above and a nitrosothiol containing acyl imidazolide is representative of the $R_{17}$ group as defined above may be prepared as outlined in FIG. 17. The 1H-purine-2,6-dione of formula 21 is converted to the acylated derivative of the formula 23 wherein p, $R_e$ and $R_f$ are defined above by reaction with an appropriate protected thiol containing activated acylating agent wherein $P^2$ is defined above. Preferred methods for the formation of acylated 1H-purine-2,6-diones are reacting the 1H-purine-2,6-dione with the preformed acid chloride or symmetrical anhydride of the protected thiol containing acid or condensing the 1H-purine-2,6-dione and protected thiol containing acid in the presence of a dehydrating agent such as DCC or EDAC HCl with a catalyst such as DMAP or HOBt. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula VIB. Alternatively, treatment of the deprotected thiol derived from compound 23 with a stoichiometric quantity of sodium nitrite in an acidic aqueous or alcoholic solution affords the compound of the formula VIB.

Figure 18:
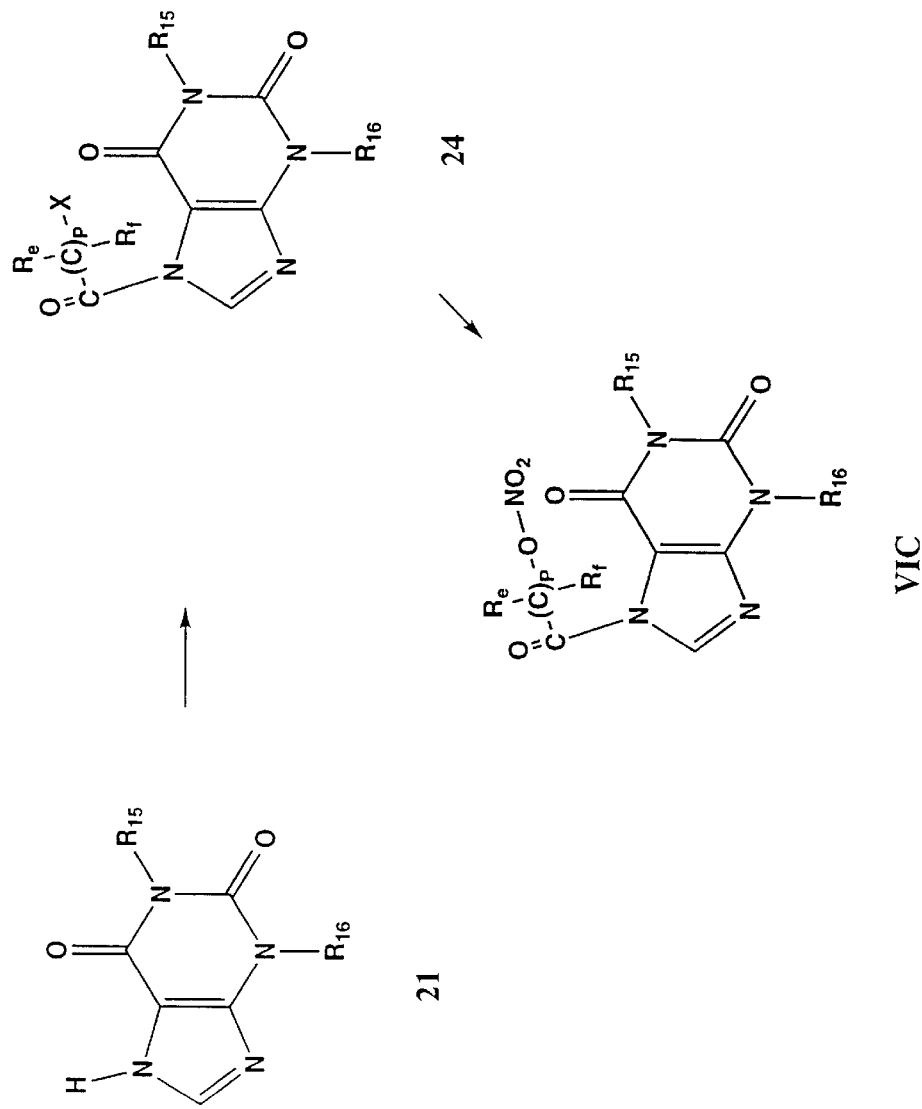
FIG. 18 shows a synthetic scheme for the preparation of nitrate containing purine-2,6-dione derivatives.

Nitro compounds of formula (VI) wherein $R_{15}$, $R_{16}$, $R_e$, $R_f$, and p are defined above and an O-nitrosated acylated 1H-purine-2,6-dione is representative of the $R_{17}$ group as defined above may be prepared as outlined in FIG. 18. The 1H-purine-2,6-dione of the formula 21 is converted to the acylated derivative of the formula 24 wherein p, $R_e$ and $R_f$ are defined above and X is a halogen by reaction with an appropriate halide containing activated acylating agent. Preferred methods for the formation of acylated 1H-purine-2,6-diones are reacting the 1H-purine-2,6-dione with the preformed acid chloride or symmetrical anhydride of the halide containing acid or condensing the 1H-purine-2,6-dione and halide containing acid in the presence of a dehydrating agent such as DCC or EDAC HCl with a catalyst such as DMAP or HOBt. Preferred halides are bromide and iodide. Reaction of the acylated 1H-purine-2,6-dione of the formula 24 with a suitable nitrating agent such as silver nitrate in an inert solvent such as acetonitrile affords the compound of formula VIC.

Another embodiment of this aspect provides processes for making compounds having structure VII and to the intermediates useful in such processes as follows.

Figure 19:
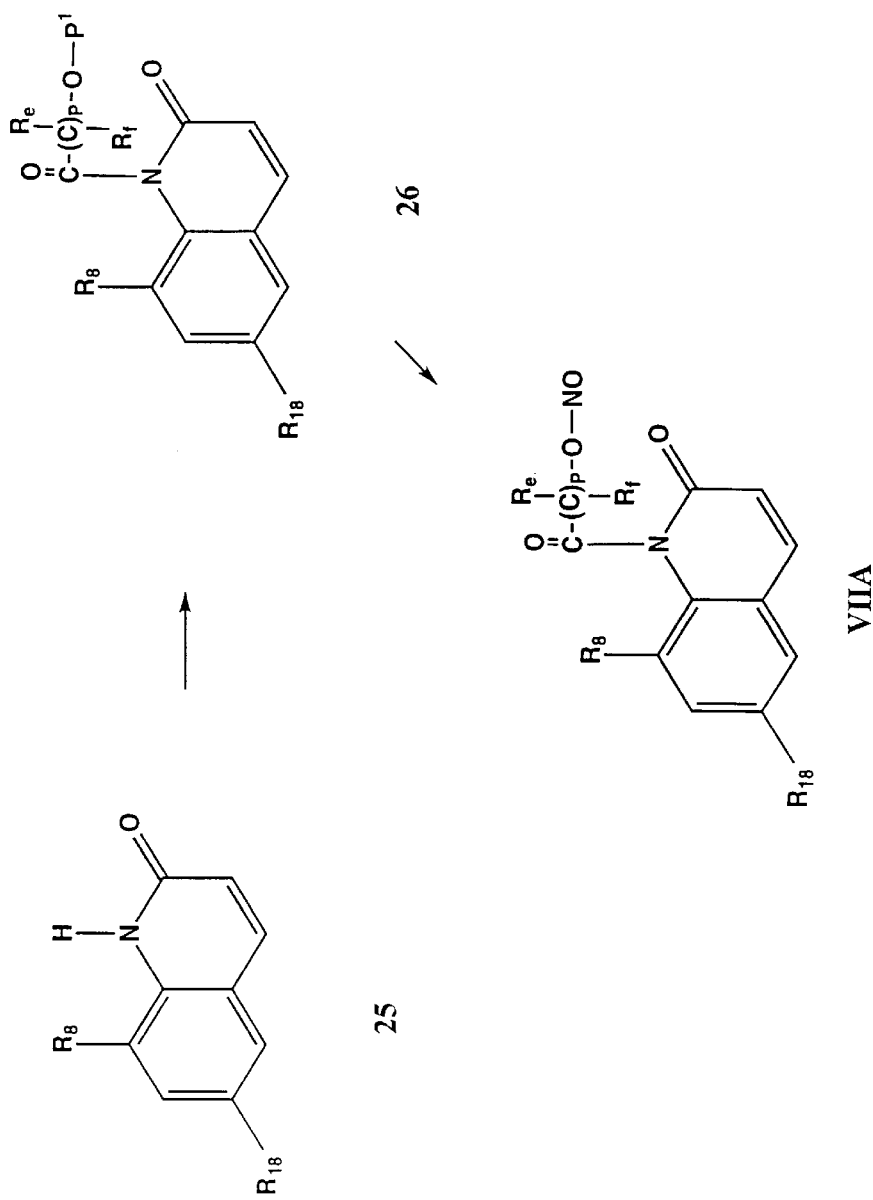
FIG. 19 shows a synthetic scheme for the preparation of nitrite containing quinoline derivatives.

Nitroso compounds of formula (VII) wherein $R_8$, $R_{18}$, $R_e$, $R_f$, and p are defined above and a nitrite containing imide is representative of the $R_4$ group as defined above may be prepared as outlined in FIG. 19. The amide nitrogen of formula 25 is converted to the imide of formula 26 wherein p, $R_e$ and $R_f$ are defined above by reaction with an appropriate protected alcohol containing activated acylating agent wherein $P^1$ is defined above. Preferred methods for the formation of imides are reacting the amide with the preformed acid chloride of the protected alcohol containing acid in the presence of pyridine at low temperature or condensing the amide and protected alcohol containing symmetrical anhydride in the presence of a catalyst such as sulfuric acid. Preferred protecting groups for the alcohol moiety are silyl ethers such as a tert-butyldimethylsilyl ether or a tertbutyldiphenylsilyl ether Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula VIIA.

Figure 20:
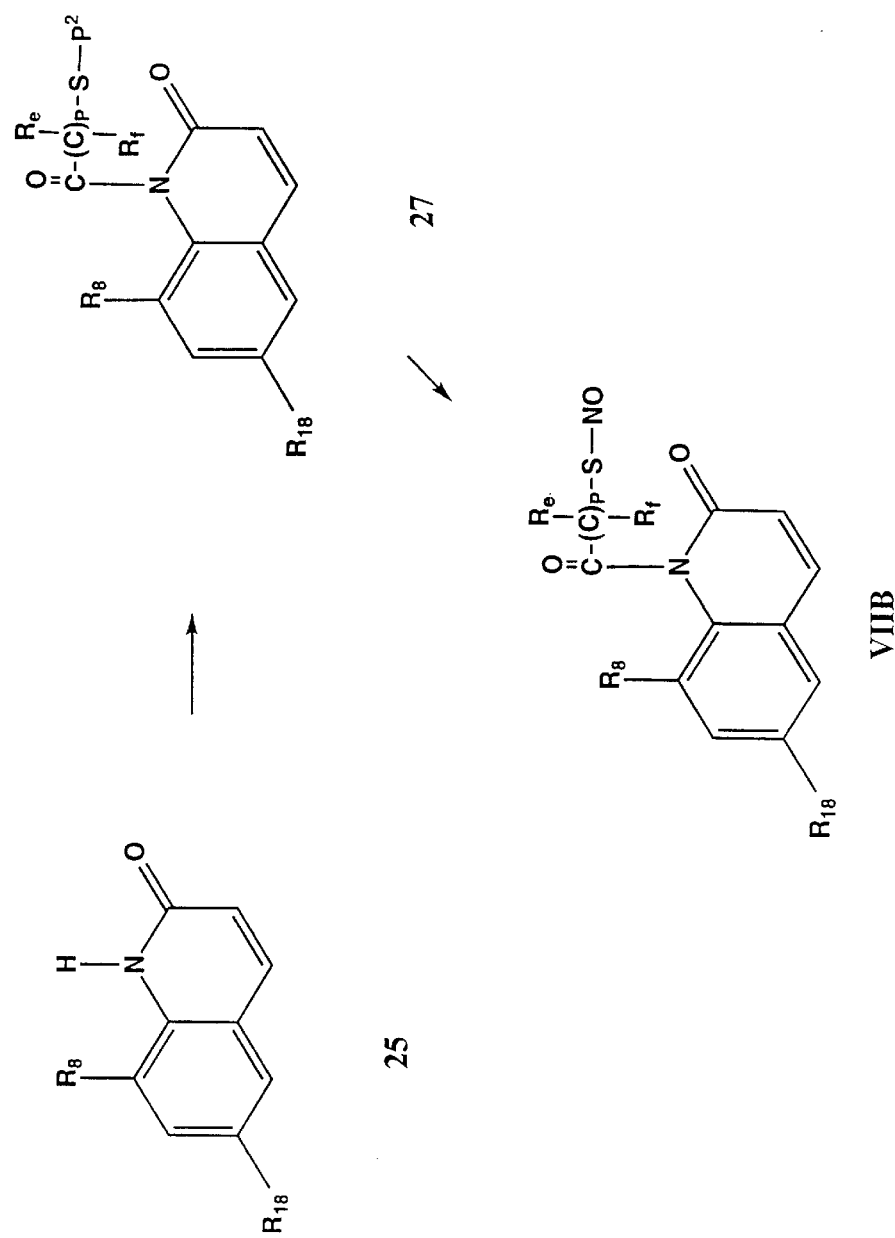
FIG. 20 shows a synthetic scheme for the preparation of nitrosothiol containing quinoline derivatives.

Nitroso compounds of formula (VII) wherein $R_8$, $R_{18}$, $R_e$, $R_f$, and p are defined above and a nitrosothiol containing imide is representative of the $R_4$ group as defined above may be prepared as outlined in FIG. 20. The amide nitrogen of formula 25 is converted to the imide of formula 27 wherein p, $R_e$ and $R_f$ are defined above by reaction with an appropriate protected thiol containing activated acylating agent wherein $P^2$ is defined above. Preferred methods for the formation of imides are reacting the amide with the preformed acid chloride of the protected thiol containing acid in the presence of pyridine at low temperature or condensing the amide and protected thiol containing symmetrical anhydride in the presence of a catalyst such as sulfuric acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically used to hydrolyze thioesters and Nmethoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula VIIB. Alternatively, treatment of the deprotected thiol derived from compound 27 with a stoichiometric quantity of sodium nitrite in an acidic aqueous or alcoholic solution affords the compound of the formula VIIB.

Figure 21:
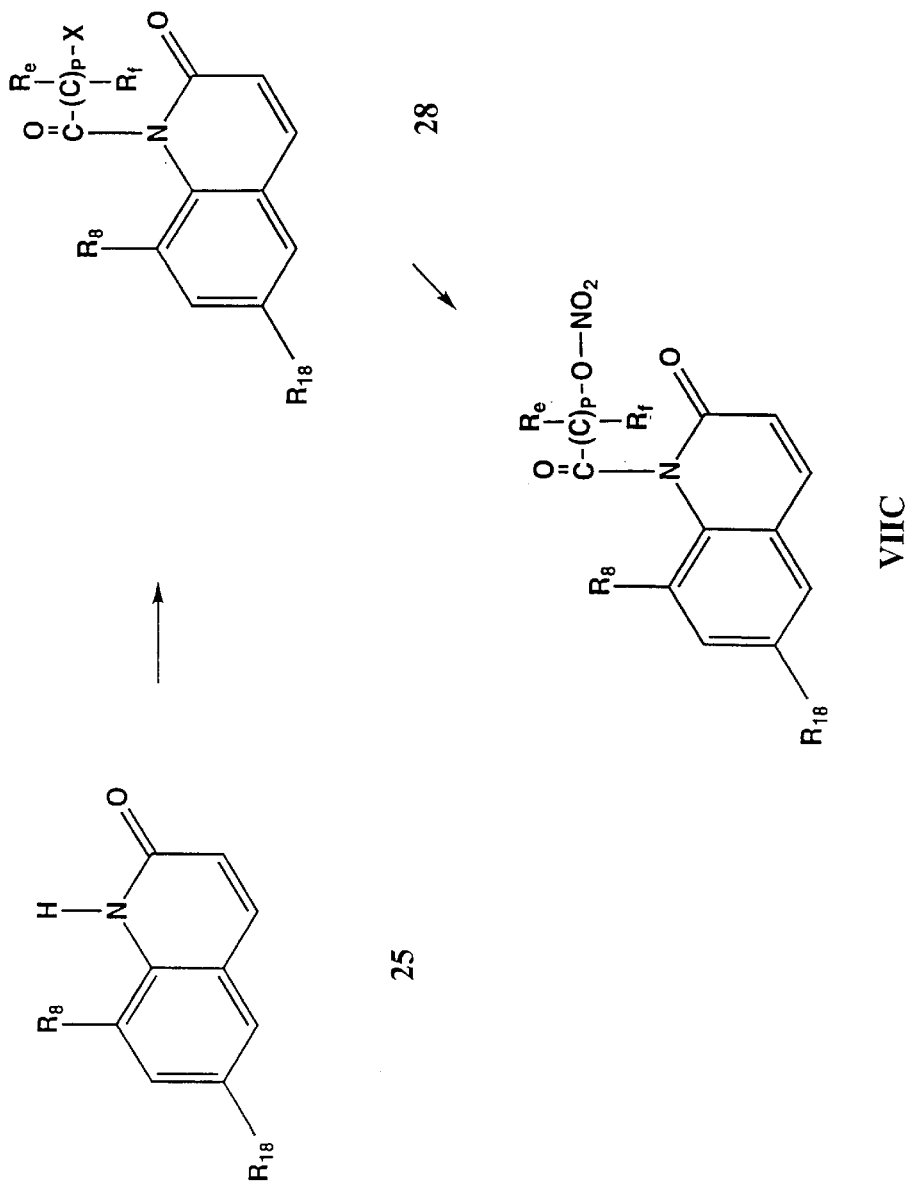
FIG. 21 shows a synthetic scheme for the preparation of nitrate containing quinoline derivatives.

Nitro compounds of formula (VII) wherein $R_8$, $R_{18}$, $R_e$, $R_f$, and p are defined above and a nitrate containing imide is representative of the $R_4$ group as defined above may be prepared as outlined in FIG. 21. The amide group of the formula 25 is converted to the imide of the formula 28 wherein p, $R_e$ and $R_f$ are defined above and X is a halogen by reaction with an appropriate halide containing activated acylating agent. Preferred methods for the formation of imides are reacting the amide with the preformed acid chloride of the halide containing acid in the presence of pyridine at low temperature or condensing the amide and halide containing symmetrical anhydride in the presence of a catalyst such as sulfuric acid. Preferred halides are bromide and iodide. Reaction of the imide of the formula 28 with a suitable nitrating agent such as silver nitrate in an inert solvent such as acetonitrile affords the compound of the formula VIIC.

Another embodiment of this aspect provides processes for making compounds having structure VIII and to the intermediates useful in such processes as follows.

Figure 22:
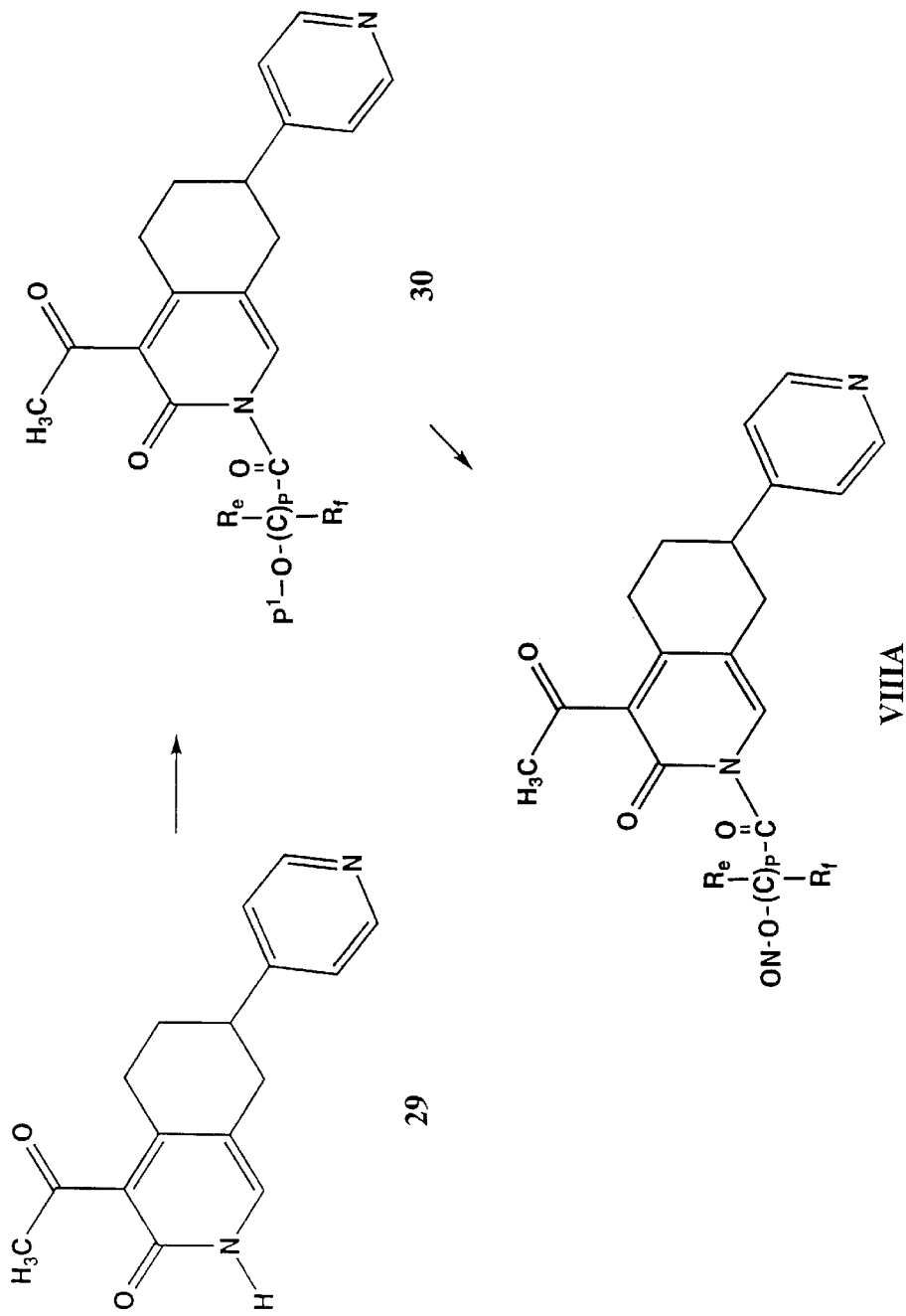
FIG. 22 shows a synthetic scheme for the preparation of nitrite containing substituted pyridine derivatives.

Nitroso compounds of formula (VIII) wherein $R_e$, $R_f$, and p are defined above and a nitrite containing imide is representative of the $R_{19}$ group as defined above may be prepared as outlined in FIG. 22. The amide nitrogen of formula 29 is converted to the imide of formula 30 wherein p, $R_e$ and $R_f$ are defined above by reaction with an appropriate protected alcohol containing activated acylating agent wherein $P^1$ is defined above. Preferred methods for the formation of imides are reacting the amide with the preformed acid chloride of the protected alcohol containing acid in the presence of pyridine at low temperature or condensing the amide and protected alcohol containing symmetrical anhydride in the presence of a catalyst such as sulfuric acid. Preferred protecting groups for the alcohol moiety are silyl ethers such as a tert-butyldimethylsilyl ether or a tert-butyldiphenylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or tri ethyl amine affords the compound of the formula VIIIA.

Figure 23:
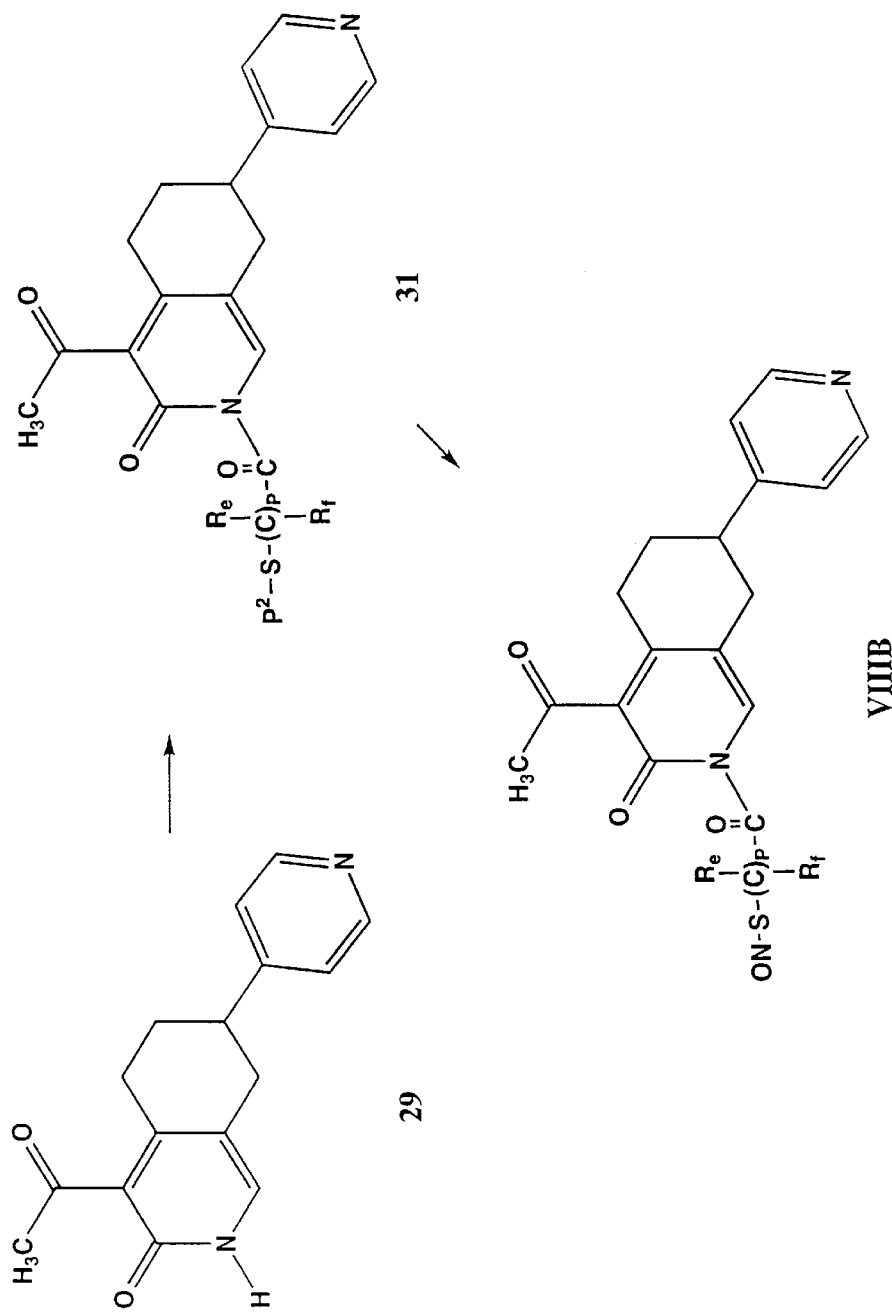
FIG. 23 shows a synthetic scheme for the preparation of nitrosothiol containing substituted pyridine derivatives.

Nitroso compounds of formula (VIII) wherein $R_e$, $R_f$, and p are defined above and a nitrosothiol containing imide is representative of the $R_{19}$ group as defined above may be prepared as outlined in FIG. 23. The amide nitrogen of formula 29 is converted to the imide of formula 31 wherein p, $R_e$ and $R_f$ are defined above by reaction with an appropriate protected thiol containing activated acylating agent wherein $P^2$ is defined above. Preferred methods for the formation of imides are reacting the amide with the preformed acid chloride of the protected thiol containing acid in the presence of pyridine at low temperature or condensing the amide and protected alcohol containing symmetrical anhydride in the presence of a catalyst such as sulfuric acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing di sulfide groups while aqueous base is typically utilized to hydrolyze thioesters and Nmethoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl di nitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula VIIB. Alternatively, treatment of the deprotected thiol derived from compound 31 with a stoichiometric quantity of sodium nitrite in an acidic aqueous or alcoholic solution affords the compound of the formula VIIIB.

Figure 24:
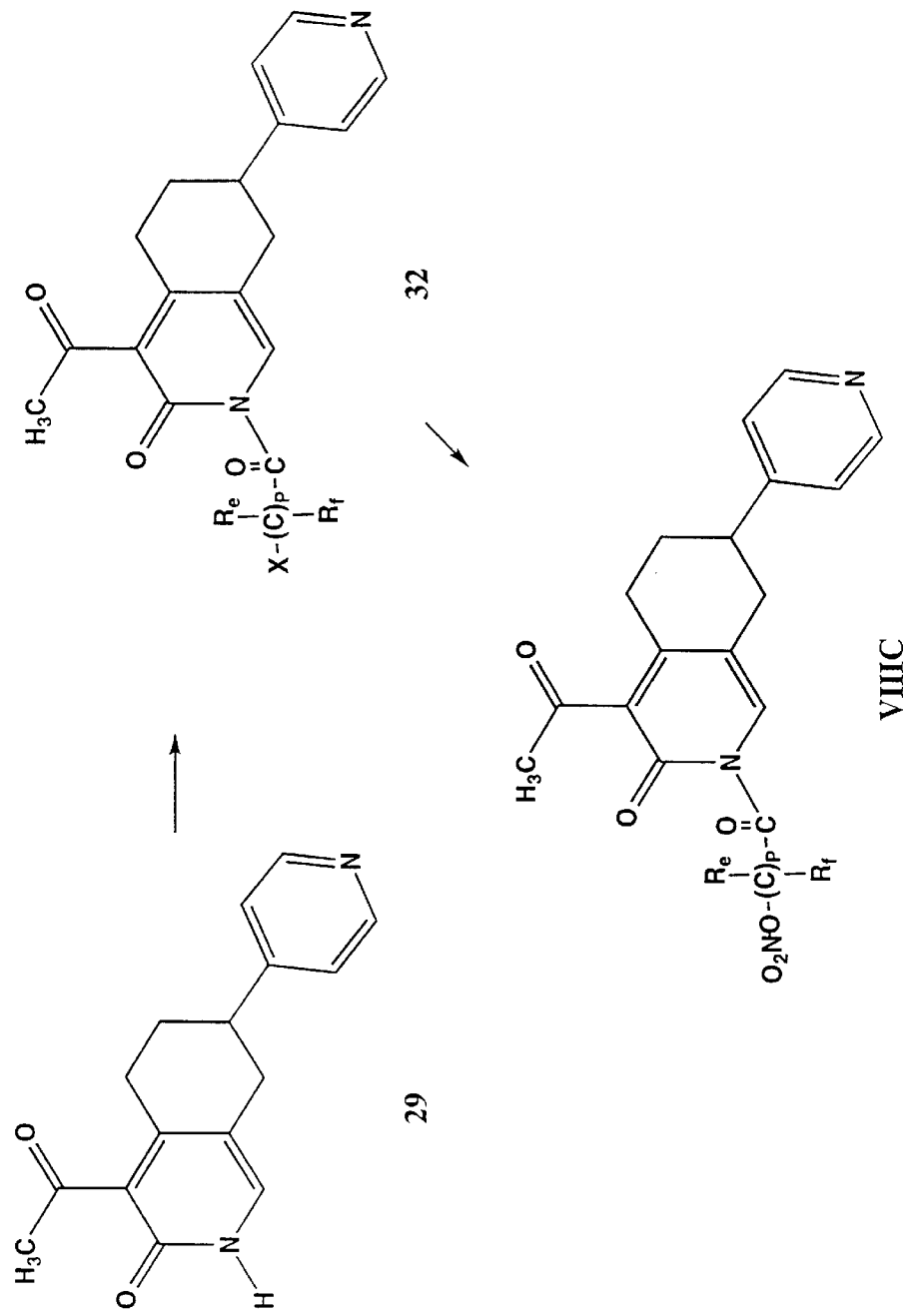
FIG. 24 shows a synthetic scheme for the preparation of nitrate containing substituted pyridine derivatives.

Nitro compounds of formula (VIII) wherein $R_e$ $R_f$, and p are defined above and a nitrate containing imide is representative of the $R_{19}$ group as defined above may be prepared as outlined in FIG. 24. The amide group of the formula 29 is converted to the imide of the formula 32 wherein p, $R_e$ and $R_f$ are defined above and X is a halogen by reaction with an appropriate halide containing activated acylating agent. Preferred methods for the formation of imides are reacting the amide with the preformed acid chloride of the halide containing acid in the presence of pyridine at low temperature or condensing the amide and halide containing symmetrical anhydride in the presence of a catalyst such as sulfuric acid. Preferred halides are bromide and iodide. Reaction of the imide of the formula 32 with a suitable nitrating agent such as silver nitrate in an inert solvent such as acetonitrile affords the compound of the formula VIIIC.

Another embodiment of this aspect provides processes for making compounds having structure IX and to the intermediates useful in such processes as follows.

Figure 25:
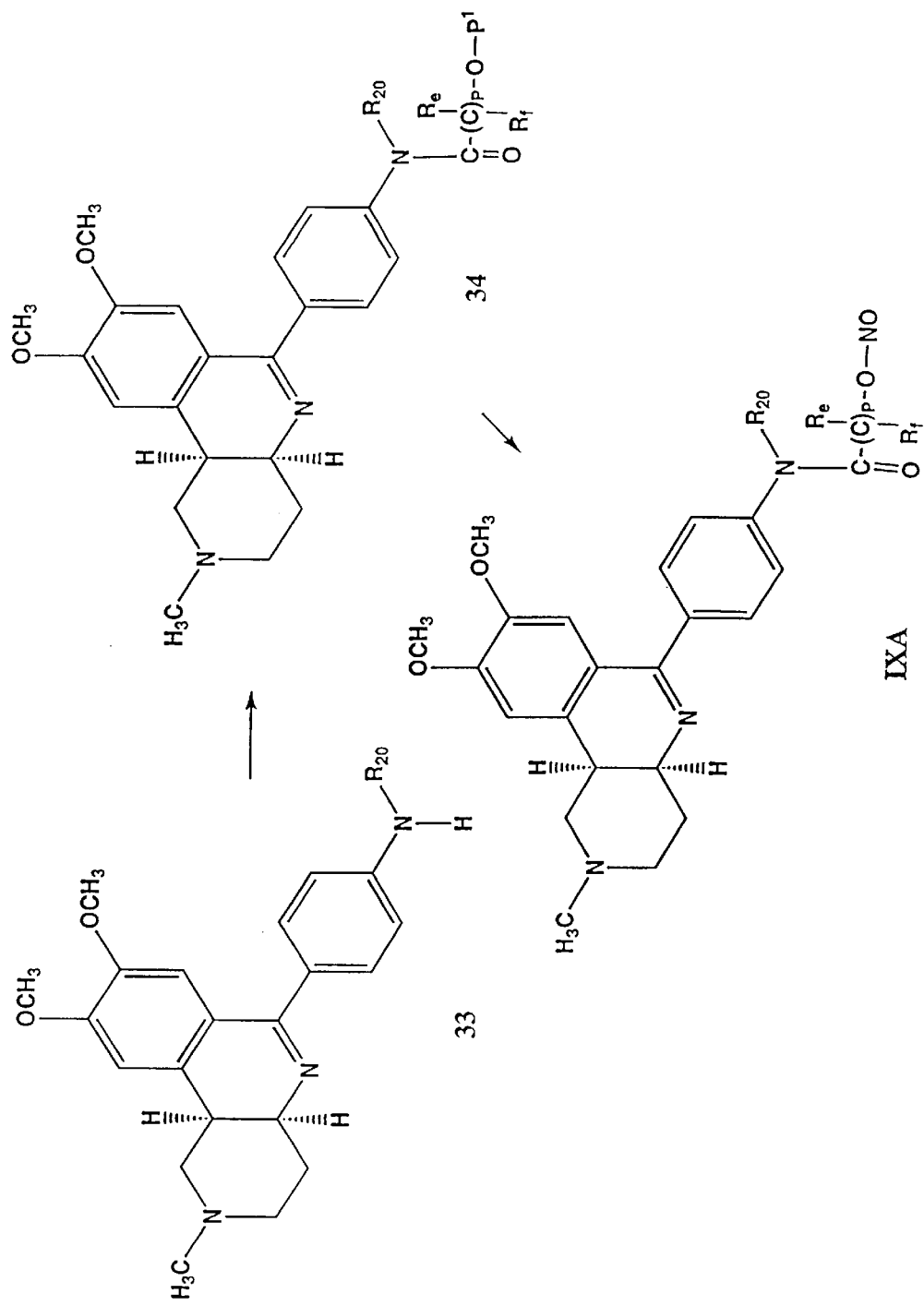
FIG. 25 shows a synthetic scheme for the preparation of nitrite containing benzo [c] [1,6] naphthyridine derivatives.

Nitroso compounds of formula (IX) wherein $R_{20}$, $R_e$, $R_f$, and p are defined above and an nitrate containing imide or sulfonimide is representative of the $R_4$ group as defined above may be prepared as outlined in FIG. 25. The amide or sulfonamide nitrogen of formula 33 is converted to the imide or sulfonimide of formula 34 wherein p, $R_e$ and $R_f$ are defined above by reaction with an appropriate protected alcohol containing activated acylating agent wherein $P^1$ is defined above. Preferred methods for the formation of imides or sulfonimides are reacting the amide or sulfonimide with the preformed acid chloride of the protected alcohol containing acid in the presence of pyridine at low temperature or condensing the amide or sulfonimide and protected alcohol containing symmetrical anhydride in the presence of a catalyst such as sulfuric acid. Preferred protecting groups for the alcohol moiety are silyl ethers such as a tert-butyldimethylsilyl ether or a tertbutyldiphenylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoro-borate in a suitable anhydrous solvent such as dichloromethane, THF, DMF, or acetonitrile with or without an amine base such as pyridine or triethylamine affords the compound of the formula IXA.

Figure 26:
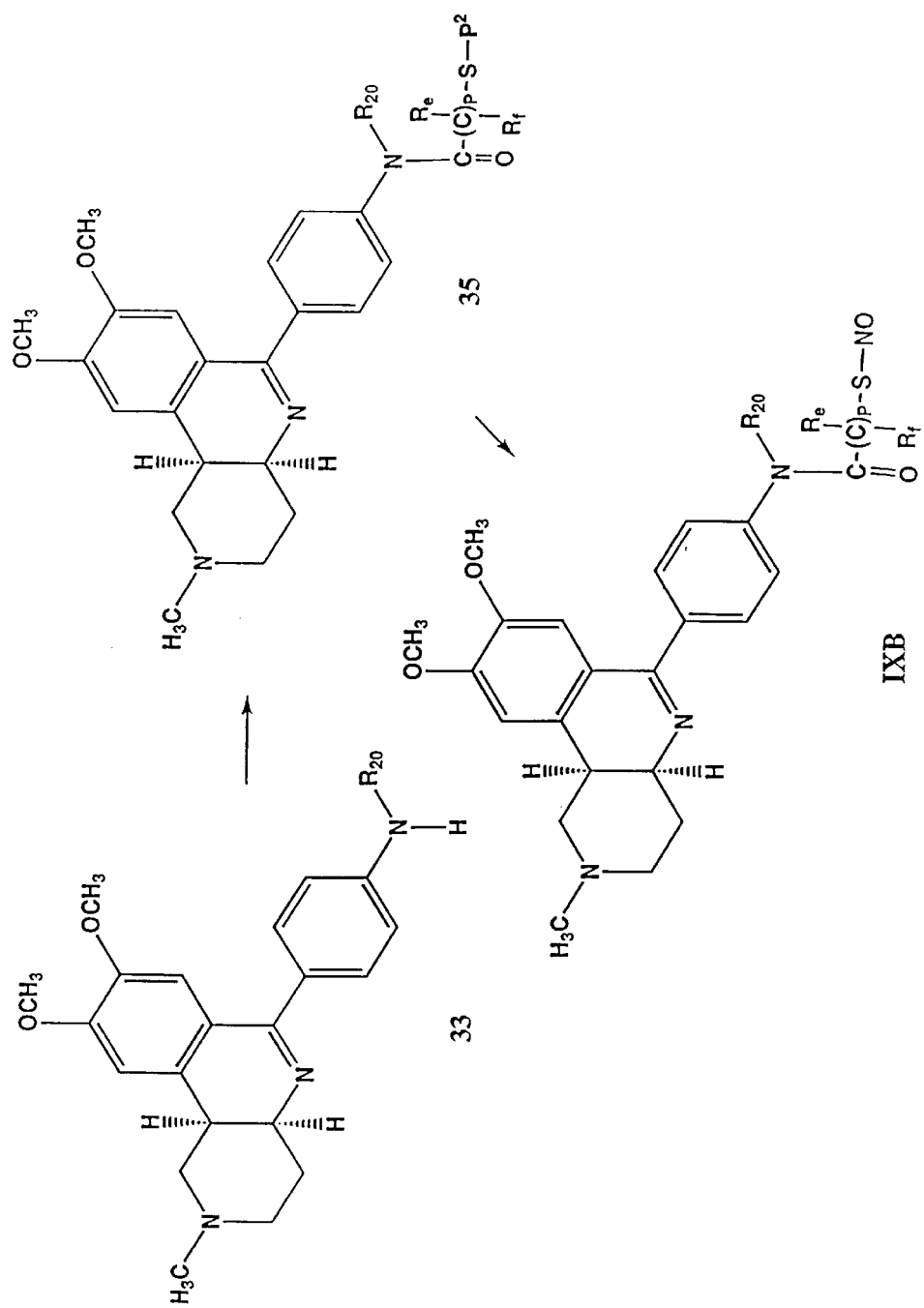
FIG. 26 shows a synthetic scheme for the preparation of nitrosothiol containing benzo[c] [1,6] naphthyridine derivatives.

Nitroso compounds of formula (IX) wherein $R_{20}$, $R_e$, $R_f$, and p are defined above and an nitrosothiol containing imide or sulfonimide is representative of the $R_4$ group as defined above may be prepared as outlined in FIG. 26. The amide or sulfonamide nitrogen of formula 33 is converted to the imide or sulfonimide of formula 35 wherein p, $R_e$ and $R_f$ are defined above by reaction with an appropriate protected thiol containing activated acylating agent wherein $P^2$ is defined above. Preferred methods for the formation of imides or sulfonimides are reacting the amide or sulfonimide with the preformed acid chloride of the protected thiol containing acid in the presence of pyridine at low temperature or condensing the amide or sulfonimide and protected thiol containing symmetrical anhydride in the presence of a catalyst such as sulfuric acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxy-benzyl thioether, a tetrahydropyranyl thioether or a 2,4,6-trimethoxybenzyl thioether. Deprotection of the thiol moiety (zinc in dilute aqueous acid, triphenylphosphine :in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as, trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula IXB. Alternatively, treatment of the deprotected thiol derived from compound 35 with a stoichiometric quantity of sodium nitrite in an acidic aqueous or alcoholic solution affords the compound of the formula IXB.

Figure 27:
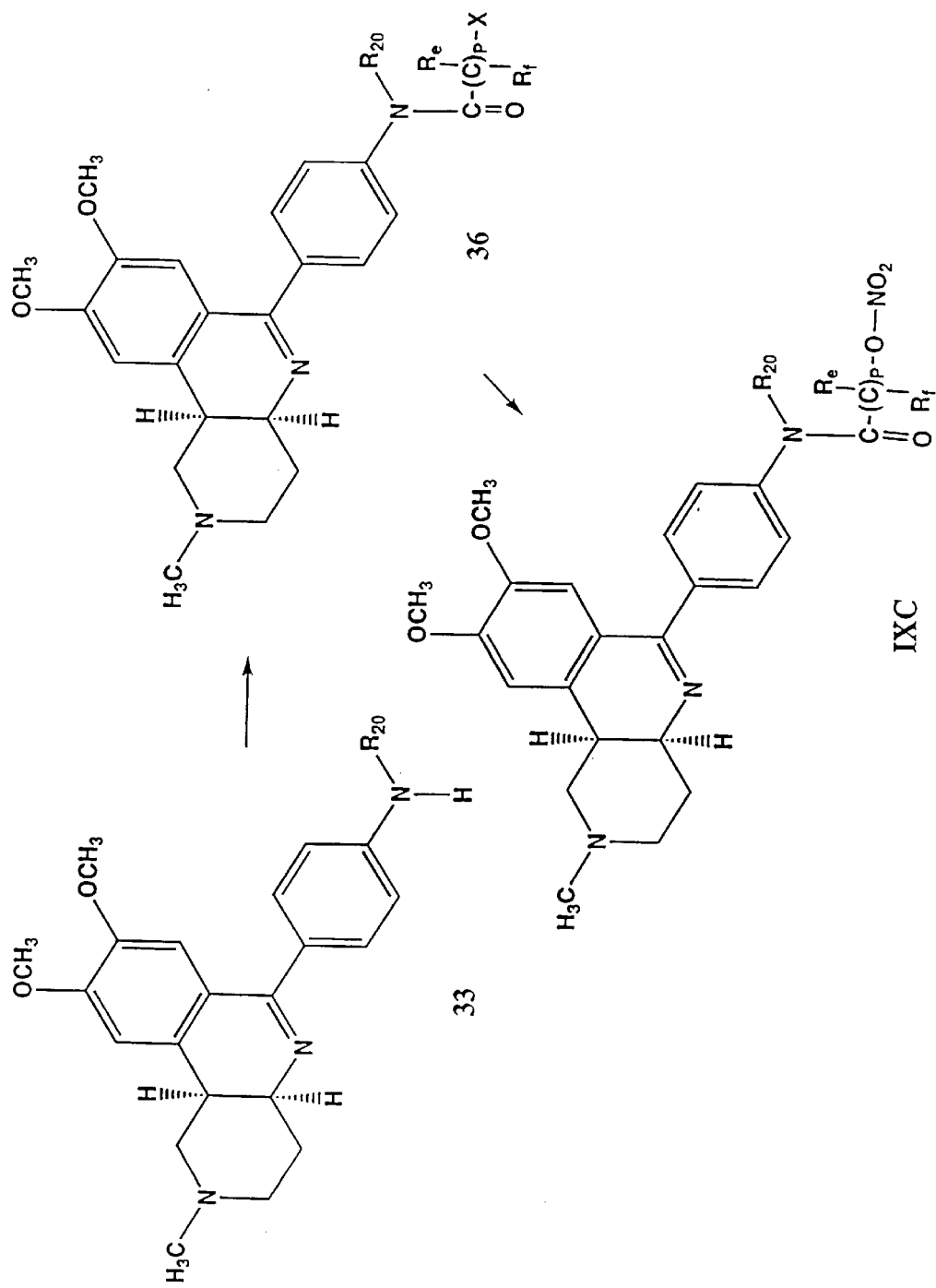
FIG. 27 shows a synthetic scheme for the preparation of nitrate containing benzo[c] [1,6] naphthyridine derivatives.

Nitro compounds of formula (IX) wherein $R_{20}$, $R_e$ $R_f$, and p are defined above and a nitrate containing imide or sulfonimide is representative of the $R_4$ group as defined above may be prepared as outlined in FIG. 27. The amide or sulfonamide group of the formula 33 is converted to the imide or sulfonimide of the formula 36 wherein p, $R_e$ and $R_f$ are defined above and X is a halogen by reaction with an appropriate halide containing activated acylating agent. Preferred methods for the formation of imides or sulfonimides are reacting the amide or sulfonamide with the preformed acid chloride of the halide containing acid in the presence of pyridine at low temperature or condensing the amide or sulfonamide and halide containing symmetrical anhydride in the presence of a catalyst such as sulfuric acid. Preferred halides are bromide and iodide. Reaction of the imide or sulfonimide of the formula 36 with a suitable nitrating agent such as silver nitrate in an inert solvent such as acetonitrile affords the compound of the formula IXC.

Another embodiment of this aspect provides processes for making compounds having structure X and to the intermediates useful in such processes as follows.

Figure 28:
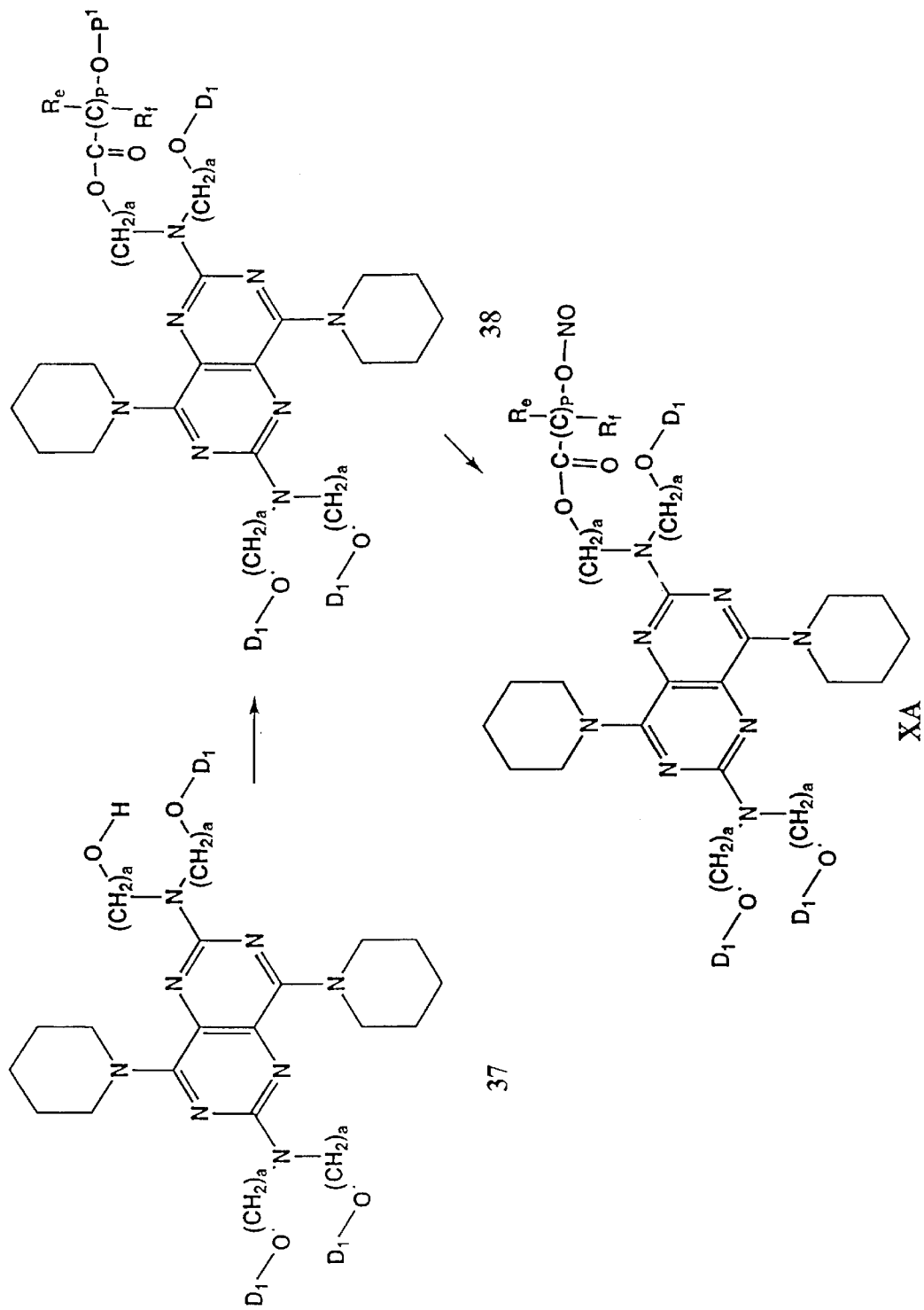
FIG. 28 shows a synthetic scheme for the preparation of nitrite containing 2,6-dihydroxyalkylamino-4,8-dipiperidino pyrimido [5,4-d] pyrimidine derivatives.

Nitroso compounds of formula (X) wherein $D_1$, $R_e$, $R_f$, and p are defined above and a nitrite containing ester is representative of the D group as defined above may be prepared according to FIG. 28. The alcohol group of formula 37 is converted to the ester of formula 38 wherein p, $R_e$ and R are defined above by reaction with an appropriate protected alcohol containing activated acylating agent wherein $P^1$ is as defined in this specification. Preferred methods for the formation of esters are reacting the alcohol with the preformed acid chloride or symmetrical anhydride of the protected alcohol containing acid or condensing the alcohol and protected alcohol containing acid with a dehydrating agent such as DCC or EDAC HCl in the presence of a catalyst such as DMAP or HOBt. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula XA.

Figure 29:
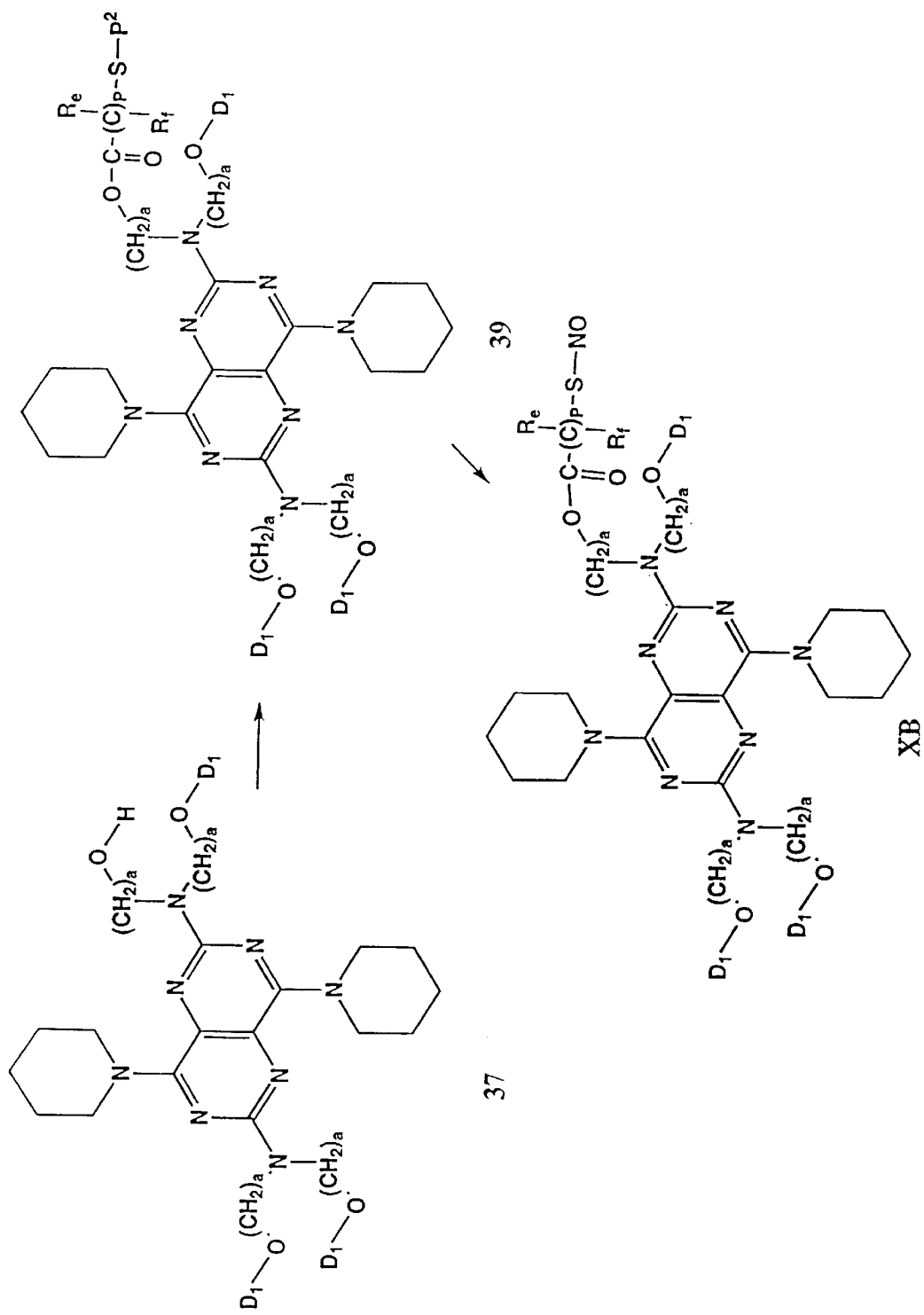
FIG. 29 shows a synthetic scheme for the preparation of nitrosothiol containing 2,6-dihydroxyalkylamino-4,8-dipiperidino pyrimido [5,4-d] pyrimidine derivatives.

Nitroso compounds of formula (X) wherein $D_1$, $R_e$ $R_f$, and p are defined above and a nitrosothiol containing ester is representative of the D group as defined above may be prepared according to FIG. 29. The alcohol group of the formula 37 is converted to the ester of the formula 39 wherein p, $R_e$ and $R_f$ are defined above by reaction with an appropriate protected thiol containing activated acylating agent wherein $P^2$ is defined above. Preferred methods for the formation of esters are reacting the alcohol with the preformed acid chloride or symmetrical anhydride of the protected thiol containing acid or condensing the alcohol and protected thiol containing acid with a dehydrating agent such as DCC or EDAC HCl in the presence of a catalyst such as DMAP or HOBt. Preferred protecting groups for the thiol moiety are as a thioester such as a thioacetate or thiobenzoate, as a disulfide, as a thiocarbamate such as N-methoxymethyl thiocarbamate, or as a thiether such as a paramethoxybenzyl thioether, a tetrahydropyranyl thioether or a S-triphenylmethyl thioether. Deprotection of the thiol moiety (zinc in dilute aqueous acid, triphenyl-phosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methyene chloride, THF, DMF, or acetonitrile with or without an amine base such as pyridine or triethylamine affords the compound of the formula XB. Alternatively, treatment of the deprotected thiol derived from compound 39 with a stoichiometric quantity of sodium nitrite in aqueous or alcoholic acid affords the compound of the formula XB.

Figure 30:
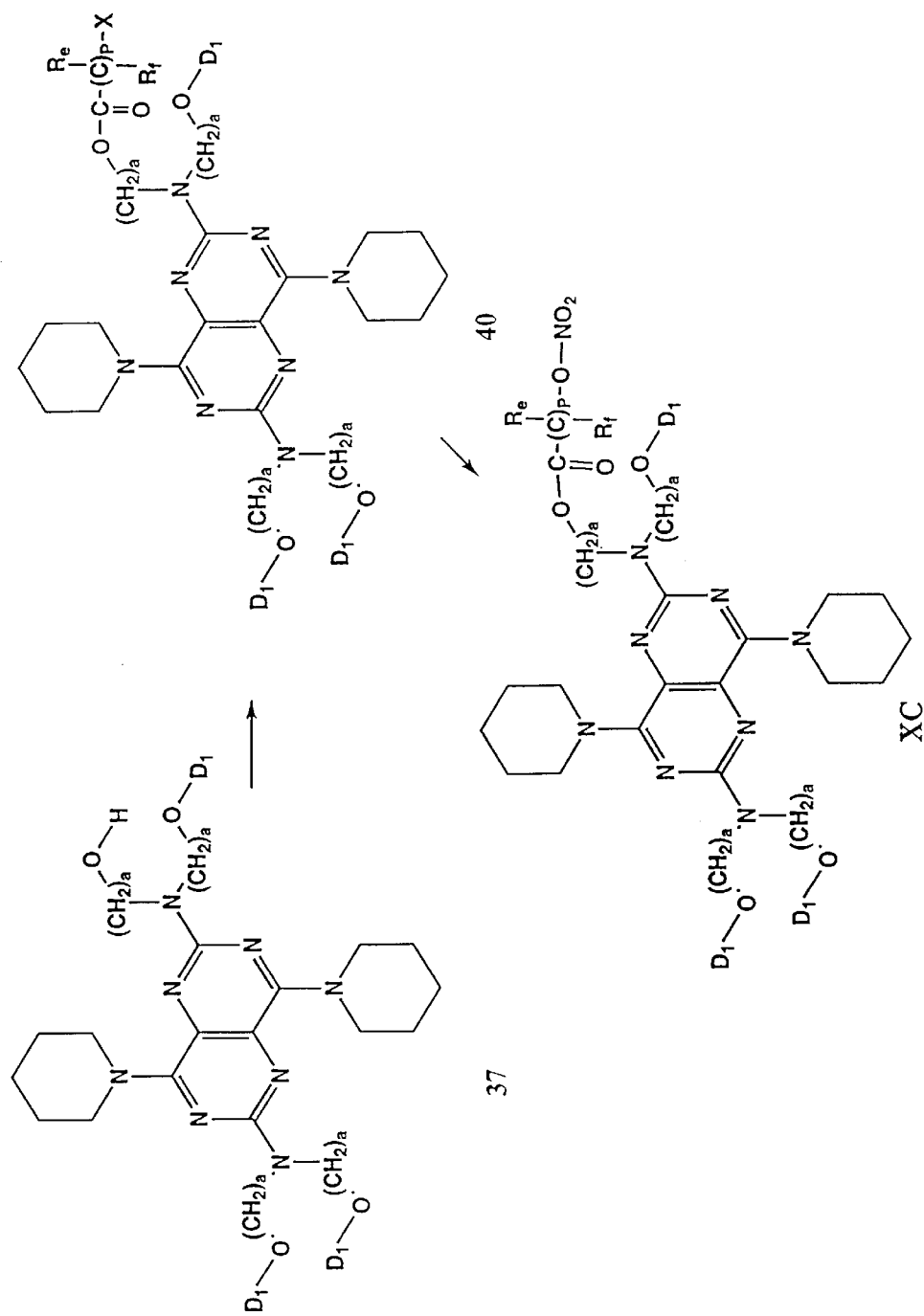
FIG. 30 shows a synthetic scheme for the preparation of nitrate containing 2,6-dihydroxyalkylamino-4,8-dipiperidino pyrimido [5,4-d] pyrimidine derivatives.

Nitro compounds of formula (X) wherein $D_1$, $R_e$, $R_f$, and p are defined above and a nitrate containing ester is representative of the D group as defined above may be prepared according to FIG. 30. The alcohol group of the formula 37 is converted to the ester of the formula 40 wherein p, $R_e$ and $R_f$ are defined above and X is a halogen by reaction with an appropriate halide containing activated acylating agent. Preferred methods for the formation of esters are reacting the alcohol with the preformed acid chloride or symmetrical anhydride of the halide containing acid or condensing the alcohol and halide containing acid with a dehydrating agent such as DCC or EDAC HCl in the presence of a catalyst such as DMAP or HOBt. Preferred halides are bromide and iodide. Reaction of the ester of the formula 40 with a suitable nitrating agent such as silver nitrate in an inert solvent such as acetonitrile affords the compound of the formula XC.

As noted above, another aspect of the invention provides a composition comprising (i) a therapeutically effective amount of at least one PDE inhibitor, which optionally can be substituted with at least one NO or $NO_2$ group or a group that stimulates endogenous production of NO or EDRF in vivo, and (ii) at least one compound that donates, transfers or releases nitrogen monoxide as a charged species, i.e., nitrosonium ($NO^+$) or nitroxyl ($NO^-$), or as the neutral species, nitric oxide (NC•) and/or at least one compound that stimulates endogenous production of NO or EDRF in vivo.

The compounds that donate, transfer or release nitric oxide or stimulate or elevate levels of endogenous EDRF can be any of those known to the art, including those mentioned and/or exemplified below.

Nitrogen monoxide can exist in three forms: $NO^-$ (nitroxyl), NO• (nitric oxide) and $NO^-$ (nitrosonium). NO• is a highly reactive short-lived species that is potentially toxic to cells. This is critical, because the pharmacological efficacy of NO depends upon the form in which it is delivered. In contrast to NO•, nitrosonium and nitroxyl do not react with $O_2$ or $O_2^-$ species. Consequently, administration of NO equivalents does not result in the generation of toxic by-products or the elimination of the active NO moiety.

Compounds contemplated for use in the invention are nitric oxide and compounds that release nitric oxide or otherwise directly or indirectly deliver or transfer nitric oxide to a site of its activity, such as on a cell membrane, in vivo. As used herein, the term "nitric oxide" encompasses uncharged nitric oxide (NO•) and charged nitric oxide species, particularly including nitrosonium ion ($NO^+$) and nitroxyl ion ($NO^-$). The reactive form of nitric oxide can be provided by gaseous nitric oxide. The nitric oxide releasing, delivering or transferring compounds, having the structure F—NO wherein F is a nitric oxide releasing, delivering or transferring moiety, include any and all such compounds which provide nitric oxide to its intended site of action in a form active for their intended purpose. As used herein the term "NO adducts" encompasses any of such nitric oxide releasing, delivering or transferring compounds, including, for example, S-nitrosothiols, S-nitrothiols, O-nitrosoalcohols, O-nitroalcohols, sydnonimines, 2-hydroxy-2-nitrosohydrazines (NONOates), (E)-alkyl-2-[(E)-hydroxyimino]-5-nitro-3-hexene amines or amides, nitrosoamines, as well a subtstates for the endogenous enzymes which synthesize nitric oxide. It is contemplated that any or all of these "NO adducts" can be mono- or poly-nitrosylated or nitrosated at a variety of naturally susceptible or artificially provided binding sites for nitric oxide or derivatives which donate or release NO.

One group of such NO adducts is the S-nitrosothiols, which are compounds that include at least one —S—NO group. Such compounds include S-nitroso-polypeptides (the term "polypeptide" includes proteins and also polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars, S-nitrosylated modified and unmodified oligonucleotides (preferably of at least 5, and more particularly 5–200 nucleotides); and an S-nitrosylated hydrocarbons where the hydrocarbon is a straight or branched, saturated or unsaturated, aliphatic or aromatic hydrocarbon; S-nitrosylated hydrocarbons having one or more substituent groups in addition to the S-nitroso group; and heterocyclic compounds. S-nitrosothiols and the methods for preparing them are described in U.S. Pat. No. 5,380,758; Oae et al., *Org. Prep. Proc. Int.*, 15(3):165–198 (1983); Loscalzo et al., *J Pharmacol. Exp. Ther.*, 249(3):726729 (1989) and Kowaluk et al., *J. Pharmacol. Exp. Ther.*, 256:1256–1264 (1990), the disclosures of which are incorporated by reference herein in their entirety.

One particularly preferred embodiment of this aspect relates to S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-homocysteine, S-nitroso-cysteine and S-nitroso-glutathione.

Suitable S-nitrosylated proteins include thiol-containing proteins (where the NO group is attached to one or more sulfur group on an amino acid or amino acid derivative thereof) from various functional classes including enzymes, such as tissue-type plasminogen activator (TPA) and cathepsin B; transport proteins, such as lipoproteins, heme proteins such as hemoglobin and serum albumin; and biologically protective proteins, such as the immunoglobulins and the cytokines. Such nitrosylated proteins are described in WO 93/09806, the disclosure of which is incorporated by reference herein in its entirety. Examples include polynitrosylated albumin where multiple thiol or other nucleophilic centers in the protein are modified.

Further examples of suitable S-nitrosothiols include the following:

(i) $CH_3(C(R_e)(R_f))_x SNO$;
(ii) $HS(C((R_e)(R_f))_x SNO$;
(iii) $ONS(C(R_e)(R_f))_x B$; and
—$H_2N$—$CH(CO_2H)$—$(CH_2)_x$—$C(O)NH$—$CH(CH_2SNO)$—$C(O)NH$—$CH_2$—$CO_2H$ wherein x equals 2 to 20; $R_e$ and $R_f$ are defined above; and B is a fluoro, a $C_1$–$C_6$ alkoxy, a cyano, a carboxamido, a cycloalkyl, an arylalkoxy, an alkylsulfinyl, an arylthio, an alkylamino, a dialkylamino, a hydroxy, a carbamoyl, a N-alkylcarbamoyl, a N,N-dialkylcarbamoyl, an amino, a hydroxyl, a carboxyl, a hydrogen, a nitro or an aryl.

Nitrosothiols can be prepared by various methods of synthesis. In general, the thiol precursor is prepared first, then converted to the S-nitrosothiol derivative by nitrosation of the thiol group with $NaNO_2$ under acidic conditions (pH is about 2.5) to yield the S-nitroso derivative. Acids which may be used for this purpose include aqueous sulfuric, acetic acid and hydrochloric acid. Alternatively, the precursor tfdol may be nitrosylated by treatment with an alkyl nitrite such as tert-butyl nitrite.

Another group of such NO adducts are those wherein the compounds donate, transfer or release nitric oxide and including compounds comprising at least one ON—O—, ON—N— or ON—C— group. The compound that includes at least one ON—N— or ON—C— group is preferably selected from the group consisting of ON—N— or ON—C— polypeptides (the term "polypeptide" includes proteins and also polyamino acids that do not possess an ascertained biological function, and derivatives thereof); ON—N— or ON—C— amino acids (including natural and synthetic amino acids and their stereoisomers and racemic mixtures); ON—N— or ON—C— sugars; ON—N— or ON—C— modified and unmodified oligonucleotides (preferably of at least 5, and more particularly 5–200 nucleotides), ON—O—, ON—N— or ON—C— hydrocarbons which can be branched or unbranched, saturated or unsaturated, aliphatic or aromatic hydrocarbons; ON—N— or ON—C— hydrocarbons having one or more substituent groups in addition to the ON—N— or ON—C— group; and ON—N— or ON—C— heterocyclic compounds.

Another group of such NO adducts is the nitrites which have an —O—NO group wherein the organic template to which the nitrite group is appended is a protein, polypeptide, amino acid, carbohydrate, branched or unbranched, saturated or unsaturated alkyl, aryl or heterocyclic compound. A preferred example is the nitrosylated form of isosorbide. Compounds in this group form S-nitrosothiol intermediates in vivo in the recipient human or other animal to be treated and can therefore include any structurally analogous precursor R—O—NO of the S-nitrosothiols described above.

Another group of such adducts are nitrates which donate, transfer or release nitric oxide and include compounds comprising at least one $O_2N$—O—, $O_2N$—N—, $O_2N$—S— or $O_2N$—C— group. Preferred among these are $O_2N$—O—, $O_2N$—N—, $O_2N$—S— or $O_2N$—C— polypeptides; $O_2N$—O—, $O_2N$—N—, $O_2N$—S— or $O_2N$—C— amino acids; $O_2N$—O—, $O_2N$—N—, $O_2N$—S— or $O_2N$—C— sugars; $O_2N$—O—, $O_2N$—N—, $O_2N$—S— or $O_2N$—C— modified and unmodified oligonucleotides; $O_2N$—O—, $O_2N$—N—, $O_2N$—S— or $O_2N$—C— hydrocarbons which can be branched or straight, saturated or unsaturated, aliphatic or aromatic hydrocarbons; $O_2N$—O—, $O_2N$—N—, $O_2N$—S— or $O_2N$—C— hydrocarbons having one or more substituent groups in addition to the $O_2N$—O—, $O_2N$—N—, $O_2N$—S— or $O_2N$—C— group; and $O_2N$—O—, $O_2N$—N—, $O_2N$—S— or $O_2N$—C— heterocyclic compounds. Preferred examples are isosorbide dinitrate and isosorbide mononitrate.

Another group of such NO adducts is the nitroso-metal compounds which have the structure $(R)_u$—A—M—$(NO)_v$. R includes polypeptides (the term "polypeptide" includes proteins and also polyamino acids that do not possess an ascertained biological function, and derivatives thereof); amino acids (including natural and synthetic amino acids and their stereoisomers and racemic mixtures and derivatives thereof); sugars; modified and unmodified oligonucleotides (preferably of at least 5, and more particularly 5–200 nucleotides); and a hydrocarbon where the hydrocarbon can be branched or straight, saturated or unsaturated, aliphatic or aromatic hydrocarbon; hydrocarbons having one or more substituent groups in addition to the A-nitroso group; and heterocyclic compounds; A is S, O, or N; u and v are each independently an integer of 1, 2 and 3, and M is a metal, preferably a transition metal. Preferred metals include iron, copper, manganese, cobalt, selenium and luthidium. Also contemplated are N-nitrosylated metal centers such as nitroprusside.

Another group of such adducts are 2-hydroxy-2-nitrosohydrazines which donate, transfer or release nitric oxide and have a $R_{61}R_{62}$—N(O—$M^+$)—NO group wherein $R_{61}$ and $R_{62}$ each independently include polypeptides, amino acids, sugars, modified and unmodified oligonucleotides, hydrocarbons where the hydrocarbon can be branched or straight, saturated or unsaturated, aliphatic or aromatic hydrocarbon, hydrocarbons having one or more substituent groups and heterocyclic compounds. $M^+$ is a metal cation, such as, for example, a Group I metal cation.

Another group of such adducts are thionitrates which donate, transfer or release nitric oxide and have the structure $R_{61}S$—$NO_2$ wherein $R_{61}$ is as described above.

The present invention is also directed to compounds that stimulate endogenous synthesis of NO or elevate levels of endogenous endothelium-derived relaxing factor (EDRF) in vivo. Such compounds include, for example, L-arginine and OH-arginine, the substrates for nitric oxide synthase, cytokines, adenosine, bradykinin, calreticulin, bisacodyl, phenolphthalein, and endothelin. EDRF is a vascular relaxing factor secreted by the endothelium, and has been identified as nitric oxide (NO) or a closely related derivative thereof. (Palmer et al, *Nature*, 327:524–526 (1987), Ignarro et al, *Proc. Natl. Acad. Sci. USA*, 84:9265–9269 (1987))

When administered in vivo, the nitric oxides may be administered in combination with pharmaceutical carriers and in dosages described herein.

The nitrosated or nitrosylated compounds of the invention are used at dose ranges and over a course of dose regimen and are administered in the same or substantially equivalent vehicles/carrier by the same or substantially equivalent oral or nasal inhalant devices as their non-nitrosated or non-nitrosylated counterparts. The nitrosated or nitrosylated compounds of the invention can also be used in lower doses and in less extensive regimens of treatment. The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound used, whether a drug delivery system is used and whether the compound is administered as part of a drug combination. Thus, the dosage regimen actually employed may vary widely and therefore may deviate from the preferred dosage regimen set forth above.

Total daily dose administered to a host in single or divided doses may be in amounts, for example, from about 1 to about 100 mg/kg body weight daily and more usually about 3 to 30 mg/kg. Dosage unit compositions may contain such amounts of submultiples thereof to make up the daily dose.

While the compounds of the invention can be administered as the sole active pharmaceutical agent, they can also be used in combination with one or more compounds which are known to be effective against the specific disease state targeted for treatment. The compositions of the invention can also be administered as described above or can be made to include one or more additional active compounds which are known to be effective against the specific disease state is targeted for treatment.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

Each of the publications, patents and patent applications described herein is hereby incorporated by reference herein in their entirety.

Various modifications of the invention, in addition to those described herein, will be apparent to one skilled in the art from the foregoing description. Such modifications are also intended to fall within the scope of the appended claims.

What is claimed is:

1. A method for treating a sexual dysfunction in an individual in need thereof comprising administering a therapeutically effective amount of a phosphodiesterase inhibitor and a compound that donates, transfers or releases nitrogen monoxide, induces the production of endogenous endothelium-derived relaxing factor, stimulates endogenous synthesis of nitrogen monoxide or is a substrate for nitric oxide synthase, wherein the phosphodiesterase inhibitor is a compound of structure III:

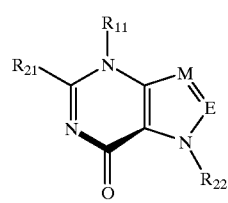

III wherein:
E is nitrogen or —CH—;
M is nitrogen or —C($R_8$)—;
$R_8$ is hydrogen or a lower alkyl;
$R_{21}$ is:

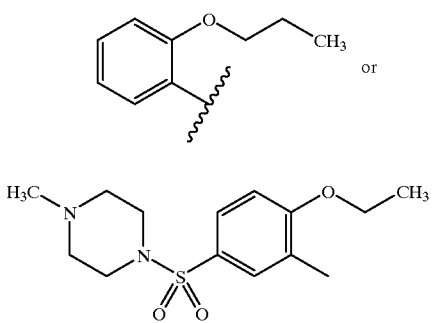

$R_{22}$ is $R_{12}$ or a lower alkyl; and
$R_{11}$ and $R_{12}$ are each independently a hydrogen.

2. The method of claim 1, wherein the compound of structure III is sildenafil.

3. The method of claim 1, wherein the compound of structure III is zaprinast.

4. The method of claim 1, wherein the compound that donates, transfers or releases nitrogen monoxide, induces the production of endogenous endothelium-derived relaxing factor, stimulates endogenous synthesis of nitrogen monoxide or is a substrate for nitric oxide synthase is an S-nitrosothiol.

5. The method of claim 4, wherein the S-nitrosothiol is S-nitroso-N-acetylcysteine, S-nitroso-captopril, S-nitroso-homocysteine, S-nitroso-cysteine or S-nitroso-glutathione.

6. The method of claim 4, wherein the S-nitrosothiol is:
(i) $CH_3(C(R_e)(R_f))_xSNO$;
(ii) $HS(C((R_e)(R_f))_xSNO$;
(iii) $ONS(C(R_e)(R_f))_xB$; or
(iv) $H_2N$—$CH(CO_2H)$—$(CH_2)_x$—$C(O)N$—$CH(CH_2SNO)$—$C(O)NH$—$CH_2$—$CO_2H$;
wherein x equals 2 to 20; $R_e$ and $R_f$ are independently a hydrogen, a lower alkyl, a haloalkyl, an alkoxy, a carboxylic acid, a carboxylic ester, a cycloalkyl, an aryl, a heteroaryl, an arylalkyl, an alkylamino, a dialkylamino, or —T—Q, or $R_e$ and $R_f$ taken together with the carbon atoms to which they are attached are a carbonyl, a heterocyclic ring, a cycloalkyl or a bridged cycloalkyl; T is a covalent bond, oxygen, sulfur or nitrogen, Q is NO or $NO_2$, and B is a fluoro, an alkoxy, a cyano, a carboxamido, a cycloalkyl, an arylalkoxy, an alkylsulfinyl, an arylthio, an alkylamino, a dialkylamino, a hydroxy, a carbamoyl, an N-alkylcarbamoyl, an N,N-dialkylcarbamoyl, an amino, a hydroxyl, a carboxyl, a hydrogen, a nitro or an aryl.

7. The method of claim 1, wherein the compound that donates, transfers or releases nitrogen monoxide, induces the production of endogenous endothelium-derived relaxing factor, stimulates endogenous synthesis of nitrogen monoxide or is a substrate for nitric oxide synthase is L-arginine or OH-arginine.

8. The method of claim 1, wherein the compound that donates, transfers or releases nitrogen monoxide, induces the production of endogenous endothelium-derived relaxing factor, stimulates endogenous synthesis of nitrogen monoxide or is a substrate for nitric oxide synthase is:

(i) a compound comprising at least one ON—O—, ON—N— or ON—C— group;
(ii) a nitroso-metal compound having the structure $(R)_u$—A—M—$(NO)_v$, wherein R is a polypeptide, an amino acid, a sugar, an oligonucleotide, a straight or branched, saturated or unsaturated, substituted or unsubstituted, aliphatic or aromatic hydrocarbon, or a heterocyclic compound; A is S, O or N; u and v are each independently an integer of 1, 2 or 3; and M is a transition metal;
(iii) a compound having the structure $R_{61}R_{62}$—N—(O—$M^+$)—NO, wherein $R_{61}$ and $R_{62}$ are each independently a polypeptide, an amino acid, a sugar, an oligonucleotide, a straight or branched, saturated or unsaturated, substituted or unsubstituted, aliphatic or aromatic hydrocarbon, or a heterocyclic compound; and
$M^+$ is a metal cation; or
(iv) a thionitrate having the structure $R_{61}$—S—$NO_2$, wherein $R_{61}$ is a polypeptide, an amino acid, a sugar, an oligonucleotide, a straight or branched, saturated or unsaturated, substituted or unsubstituted, aliphatic or aromatic hydrocarbon, or a heterocyclic compound.

9. The method of claim 8, wherein the compound comprising at least one ON—O—, ON—N— or ON—C— group is an ON—N— polypeptide, an ON—C-polypeptide, an ON—N-amino acid, an ON—C-amino acid, an ON—C-sugar, an ON—N-sugar, an ON—N-oligonucleotide, an ON—C-oligonucleotide, a straight or branched, saturated or unsaturated, substituted or unsubstituted, aliphatic or aromatic ON—N-hydrocarbon, a straight or branched, saturated or unsaturated, substituted or unsubstituted, aliphatic or aromatic ON—C-hydrocarbon, a straight or branched, saturated or unsaturated, aliphatic or aromatic ON—O-hydrocarbon, an ON—N-heterocyclic compound, or an ON—C-heterocyclic compound.

10. The method of claim 1, wherein the compound that donates, transfers or releases nitrogen monoxide, induces the production of endogenous endothelium-derived relaxing factor, stimulates endogenous synthesis of nitrogen monoxide or is a substrate for nitric oxide synthase is a compound comprising at least one $O_2N$—O—, $O_2N$—N—, $O_2N$—S— or $O_2N$—C-group.

11. The method of claim 10, wherein the compound comprising at least one $O_2N$—O—, $O_2N$—N—, $O_2N$—S— or $O_2N$—C— group is an $O_2N$—O-polypeptide, an $O_2N$-N—polypeptide, an $O_2N$—S-polypeptide, an $O_2N$—C-polypeptide, an $O_2N$—O-amino acid, an $O_2N$—N-amino acid, an $O_2N$—S-amino acid, an $O_2N$—C-amino acid, an $O_2N$—O-sugar, an $O_2N$—N-sugar, an $O_2N$—S-sugar, an $O_2N$—C-sugar, an $O_2N$—O-oligonucleotide, an $O_2N$—N-oligonucleotide, an $O_2N$—S-oligonucleotide, an $O_2N$—C-oligonucleotide, a straight or branched, saturated or unsaturated, substituted or unsubstituted, aliphatic or aromatic $O_2N$—O-hydrocarbon, a straight or branched, saturated or unsaturated, substituted or unsubstituted, aliphatic or aromatic $O_2N$—N-hydrocarbon, a straight or branched, saturated or unsaturated, substituted or unsubstituted, aliphatic or aromatic $O_2N$—S-hydrocarbon, a straight or branched, saturated or unsaturated, substituted or unsubstituted, aliphatic or aromatic $O_2N$—C-hydrocarbon, an $O_2N$—O-heterocyclic compound, an $O_2N$—N-heterocyclic compound, an $O_2N$—S-heterocyclic compound or an $O_2N$—C-heterocyclic compound.

12. The method of claim 1, wherein the compound that donates, transfers or releases nitrogen monoxide, induces the production of endogenous endothelium-derived relaxing factor, stimulates endogenous synthesis of nitrogen monoxide or is a substrate for nitric oxide synthase is present in a one to ten fold molar excess with respect to the phosphodiesterase inhibitor.

13. The method of claim 1, wherein the compound that donates, transfers or releases nitrogen monoxide donates, transfers or releases nitrogen monoxide as at least one of NO⁺, NO⁻ or NO•.

14. The method of claim 1, further comprising administering a pharmaceutically acceptable carrier.

15. The method of claim 1, wherein the individual is female.

16. The method of claim 1, wherein the individual is male.

17. The method of claim 1, wherein the phosphodiesterase inhibitor and the compound that donates, transfers or releases nitrogen monoxide, induces the production of endogenous endothelium-derived relaxing factor, stimulates endogenous synthesis of nitrogen monoxide or is a substrate for nitric oxide synthase are administered in the form of a composition.

18. The method of claim 1, wherein the phosphodiesterase inhibitor and the compound that donates, transfers or releases nitrogen monoxide, induces the production of endogenous endothelium-derived relaxing factor, stimulates endogenous synthesis of nitrogen monoxide or is a substrate for nitric oxide synthase are administered separately.

19. The method of claim 1, wherein the phosphodiesterase inhibitor and the compound that donates, transfers or releases nitrogen monoxide, induces the production of endogenous endothelium-derived relaxing factor, stimulates endogenous synthesis of nitrogen monoxide or is a substrate for nitric oxide synthase are administered orally.

20. A composition comprising a therapeutically effective amount of sildenafil and an S-nitrosothiol.

21. The composition of claim 20, wherein the S-nitrosothiol is S-nitroso-N-acetylcysteine, S-nitroso-captopril, S-nitroso-homocysteine, S-nitroso-cysteine or S-nitroso-glutathione.

22. The composition of claim 21, wherein the S-nitrosothiol is S-nitroso-glutathione.

23. The composition of claim 20, wherein the S-nitrosothiol is:
  (i) $CH_3(C(R_e)(R_f))_x SNO$;
  (ii) $HS(C((R_e)(R_f))_x SNO$;
  (iii) $ONS(C(R_e)(R_f))_x B$; or
  (iv) $H_2N—CH(CO_2H)—(CH_2)_x—C(O)NH—CH(CH_2SNO)—C(O)NH—CH_2—CO_2H$;

wherein x equals 2 to 20; $R_e$ and $R_f$ are independently a hydrogen, a lower alkyl, a haloalkyl, an alkoxy, a carboxylic acid, a carboxylic ester, a cycloalkyl, an aryl, a heteroaryl, an arylalkyl, an alkylamino, a dialkylamino, or —T—Q, or $R_e$ and $R_f$ taken together with the carbon atoms to which they are attached are a carbonyl, a heterocyclic ring, a cycloalkyl or a bridged cycloalkyl; T is a covalent bond, oxygen, sulfur or nitrogen, Q is NO or $NO_2$, and B is a fluoro, an alkoxy, a cyano, a carboxamido, a cycloalkyl, an arylalkoxy, an alkylsulfinyl, an arylthio, an alkylamino, a dialkylamino, a hydroxy, a carbamoyl, an N-alkylcarbamoyl, an N,N-dialkylcarbamoyl, an amino, a hydroxyl, a carboxyl, a hydrogen, a nitro or an aryl.

24. The composition of claim 20 further comprising a pharmaceutically acceptable carrier.

25. The composition of claim 20, wherein the composition is in an orally administerable form.

26. A kit comprising the composition of claim 20.

27. A kit comprising a therapeutically effective amount of sildenafil and an S-nitrosothiol.

28. The kit of claim 27, wherein the sildenafil and the S-nitrosothiol are in the form of a composition in the kit or are separate components in the kit.

* * * * *